(12) United States Patent  (10) Patent No.: US 8,097,732 B2
Chou et al.  (45) Date of Patent: Jan. 17, 2012

(54) 1-ARYLPYRAZOLES AND THEIR USE AS PESTICIDE

(75) Inventors: David T. Chou, Raleigh, NC (US); Michael Maier, Frankfurt (DE); Friederike Petry, Lauterbach (DE); Werner Knauf, Bad Bergfabein (DE)

(73) Assignee: Merial Limited, Duluth, GA (US)

( * ) Notice: Subject to any disclaimer, the term of this patent is extended or adjusted under 35 U.S.C. 154(b) by 1040 days.

(21) Appl. No.: 11/764,255

(22) Filed: Jun. 18, 2007

(65) Prior Publication Data

US 2008/0132558 A1  Jun. 5, 2008

Related U.S. Application Data

(63) Continuation-in-part of application No. PCT/EP2005/012973, filed on Dec. 3, 2005.

(30) Foreign Application Priority Data

Dec. 18, 2004  (EP) .................................... 04030064

(51) Int. Cl.
  *C07D 231/00* (2006.01)
  *A61K 31/415* (2006.01)
(52) U.S. Cl. .................................... 548/365.7; 514/406
(58) Field of Classification Search ............... 548/365.7; 514/406
  See application file for complete search history.

(56) References Cited

FOREIGN PATENT DOCUMENTS

| DE | 19518054 A1 | | 9/1996 |
|---|---|---|---|
| DE | 10014761 | * | 9/2001 |
| WO | WO9840359 A1 | | 9/1998 |

\* cited by examiner

*Primary Examiner* — Rita Desai
*Assistant Examiner* — John Mabry
(74) *Attorney, Agent, or Firm* — Judy Jarecki-Black; John Ezcurra; Merial Limited

(57) ABSTRACT

Disclosed are compounds of formula (I) or pesticidally acceptable salts thereof, wherein, for example, W is =N—, =CH—, =CR$^7$— or =C(NR$^8$R$^9$)—, R$^7$ is halogen, R$^8$ and R$^9$ are independently of one another hydrogen, alkyl, alkenyl, alkynyl, cycloalkyl, aryl, heterocyclyl, aralkyl or heterocyclylalkyl, R$^1$ is cyano, halogen, haloalkyl or CS NH$_2$, R$^2$ is alkyl or cycloalkyl, R$^3$ is hydrogen, alkyl or cycloalkyl, R$^4$ is hydrogen, alkyl or cycloalkyl, R$^5$ is haloalkyl, haloalkoxy, halogen or —SF$_5$, R$^6$ is hydrogen, halogen, haloalkyl, nitro or NR$^{16}$R$^{17}$, R$^{16}$ and R$^{17}$ are independently of one another hydrogen, alkyl, alkenyl, alkynyl, cycloalkyl, aryl, heterocyclyl, aralkyl or heterocyclylalkyl, X is —S—, —SO—, or —SO$_2$—, Y is —O—, —S—, —SO—, or SO$_2$—, Z is hydrogen, halogen, alkyl, alkenyl, alkynyl, cycloalkyl, aryl, heterocyclyl, aralkyl, heterocyclylalkyl or NR$^{18}$R$^{19}$, and R$^{18}$ and R$^{19}$ are hydrogen, alkyl, alkenyl, alkynyl, cycloalkyl, aryl, heterocyclyl, aralkyl, heterocyclylalkyl. These compounds can be used for controlling pests, especially by treatment of domestic animals.

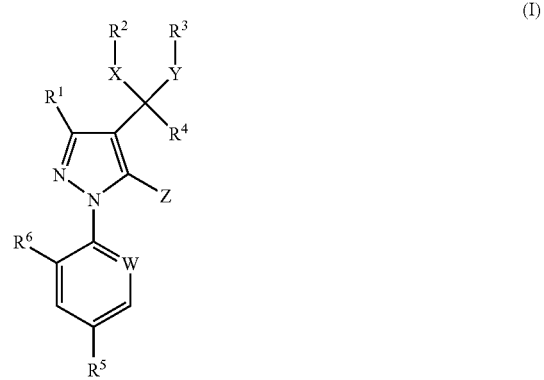

26 Claims, No Drawings

1-ARYLPYRAZOLES AND THEIR USE AS PESTICIDE

This application is a continuation-in-part application of international patent application Serial. No. PCT/EP2005/ 12973 filed Dec. 3, 2005, which published as PCT Publication No. WO 2006/063700 on Jun. 22, 2006, which claims benefit of European patent application Serial No. 04030064.2 filed Dec. 18, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention. It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. The embodiments of the present invention are disclosed herein or are obvious from and encompassed by, the detailed description. The detailed description, given by way of example, but not intended to limit the invention solely to the specific embodiments described, may best be understood in conjunction with the accompanying drawings.

The invention relates to novel 1-aryl-pyrazole derivatives, processes for their preparation, to compositions thereof, and to their use for the control of pests (including arthropods and helminths).

The control of insects, arachnids and helminths with 1-arylpyrazole compounds has been described in several documents, for example in WO-A-87/03781, EP-A-295,117, U.S. Pat. Nos. 6,069,157 and 4,695,308.

Furthermore, EP-A-846,686 discloses 1-phenyl-pyrazol derivatives and their use as parasiticidal agents.

In JP-A-08/311,036 pyrazole derivatives for insect pest control are disclosed which possess in the 4-position of the pyrazole ring a carbon substituent carrying heteroatoms.

WO-A-01/64,651 discloses 4-thiomethylpyrazoles as pesticides.

DE-A-34 23 101 discloses 5-amino-4-heterocyclyl-1-phenylpyrazole derivatives possessing herbicidal or plant growth regulating activity.

Finally, JP-A-11/171,702 discloses the control pest of angiosperm other than rice by treatment with a selected agrochemical compound. Besides other compounds, pyrazole derivatives can be used.

However, since modern pesticides must meet a wide range of demands, for example regarding level, duration and spectrum of action, use spectrum, toxicity, combination with other active substances, combination with formulation auxiliaries or synthesis, and since the occurrence of resistances is possible, the development of such substances can never be regarded as concluded, and there is constantly a high demand for novel compounds which are advantageous over the known compounds, at least as far as some aspects are concerned.

It is an object of the present invention to provide new chemical compounds which can be used in pesticidal formulation for the treatment of mammals and plants, preferably for the treatment of animals.

It is another object of the present invention to provide new pesticidal formulations which can be applied to animals advantageously in oral form so as to prevent the possible contamination of humans or the surrounding environment.

Another object of the invention is to provide new pesticides which may be used in lower dose than existing pesticides.

Another object of the invention is to provide new pesticides which are substantially non-emetic.

Another object of the invention is to provide new pesticides which are safer to the user and the environment.

Still another object of the invention is to provide new pesticides which provide effective pest control over an extended period with a single oral application.

These objects are met in whole or in part by the present invention.

The present invention provides a compound of formula I or a pesticidally acceptable salt thereof, wherein

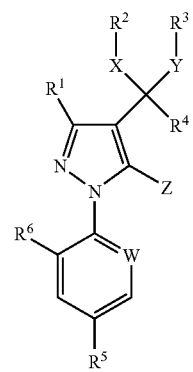

(I)

W is =N—, =CH—, =CR$^7$— or =C(NR$^8$R$^9$)—,

R$^7$ is halogen, alkyl or haloalkyl,

R$^8$ and R$^9$ are independently of one another hydrogen, alkyl, alkenyl, alkynyl, cycloalkyl, aryl, heterocyclyl, aralkyl or heterocyclylalkyl, or one of R$^8$ or R$^9$ are —CO—R$^{8a}$, —CO—O—R$^{9a}$, —SO—R$^{8a}$ or —SO$_2$R$^{8a}$, or R$^8$ and R$^9$ together with the attached N-atom form a five- to eight-membered heterocyclic ring which optionally contains an additional oxygen, sulfur or nitrogen atom in the ring or R$^8$ and R$^9$ together with the attached N-atom form an imine group —N=CR$^{8b}$R$^{9b}$ or an iminoether group —N=CR$^{8b}$(OR$^{9b}$), R$^{8a}$ and R$^{9a}$ are alkyl, cycloalkyl, aryl, heterocyclyl, aralkyl or heterocyclylalkyl, R$^{8b}$ is hydrogen, alkyl, cycloalkyl, aryl, heterocyclyl, aralkyl or heterocyclylalkyl, R$^{9b}$ is alkyl, cycloalkyl, aryl, heterocyclyl, aralkyl or heterocyclylalkyl, which groups R$^8$, R$^9$, R$^{8a}$, R$^{9a}$, R$^{8b}$, R$^{9b}$ and heterocyclic ring forming groups R$^8$ and R$^9$ independently of one another are optionally substituted by one or more halogen, hydroxyl, oxo, cyano, nitro, alkyl, haloalkyl, alkoxy, haloalkoxy, alkylthio, cycloalkyl, aryl, heterocyclyl, aralkyl or heterocyclylalkyl groups or by amino, which is optionally substituted by alkyl, alkenyl, alkynyl, aryl or heteroaryl groups;

$R^1$ is cyano, halogen, haloalkyl, —CS—NH$_2$ or C(=NR$^{10}$)S(O)$_n$R$^{11}$, $R^{10}$ is hydrogen, alkyl, alkenyl, alkynyl, cycloalkyl, aryl, heterocyclyl, aralkyl, heterocyclylalkyl, —CO—O—R$^{12}$, —CO—R$^{13}$, —SO—R$^{14}$, —SO$_2$—R$^{15}$, $R^{11}$ is alkyl, alkenyl, alkynyl, cycloalkyl, aryl, heterocyclyl, aralkyl or heterocyclylalkyl, $R^{12}$, $R^{13}$, $R^{14}$ and $R^{15}$ are alkyl, haloalkyl, alkenyl, alkynyl, cycloalkyl, aryl, heterocyclyl, aralkyl or heterocyclylalkyl, which groups $R^{10}$, $R^{12}$, $R^{13}$, $R^{14}$ and $R^{15}$ are optionally substituted by one or more halogen, hydroxyl, oxo, nitro, cyano, amino, alkyl, haloalkyl, alkoxy, haloalkoxy, alkylthio, cycloalkyl, aryl, heterocyclyl or aralkyl groups, $R^2$ is alkyl, alkenyl, alkynyl, cycloalkyl, aryl, heterocyclyl, aralkyl or heterocyclylalkyl, which group $R^2$ is optionally substituted by one or more halogen, hydroxyl, oxo, alkyl, haloalkyl, alkoxy, haloalkoxy, alkylthio, cycloalkyl, aryl, heterocyclyl, aralkyl or heterocyclylalkyl groups, $R^3$ is hydrogen, alkyl, alkenyl, alkynyl, cycloalkyl, aryl, heterocyclyl, aralkyl or heterocyclylalkyl, which group $R^3$ is optionally substituted by one or more halogen, hydroxyl, oxo, alkyl, haloalkyl, alkoxy, haloalkoxy, alkylthio, cycloalkyl, aryl, heterocyclyl, aralkyl or heterocyclylalkyl groups, or $R^2$ and $R^3$ can be linked together to form a five to nine membered heterocyclic saturated or unsaturated ring system with up to total of three ring heteroatoms selected from N, O and/or S, wherein at least one ring heteroatom is S in oxidized or non-oxidized state, and which heterocyclic ring system optionally contains condensed at two adjacent C-atoms additional carbocyclic and/or heterocyclic saturated and/or unsaturated ring systems;

$R^4$ is hydrogen, alkyl, alkenyl, alkynyl or cycloalkyl, which group $R^4$ is optionally substituted by one or more halogen, hydroxyl, oxo, alkyl, haloalkyl, alkoxy, haloalkoxy, alkylthio, cycloalkyl, aryl, heterocyclyl, aralkyl or heterocyclylalkyl groups, $R^5$ is haloalkyl, haloalkoxy, halogen or —SF$_5$, and $R^6$ is hydrogen, halogen, haloalkyl, nitro or —NR$^{16}$R$^{17}$, $R^{16}$ and $R^{17}$ are independently of one another hydrogen, alkyl, alkenyl, alkynyl, cycloalkyl, aryl, heterocyclyl, aralkyl, heterocyclylalkyl, —CO—O—R$^{12}$, —CO—R$^{13}$, —SO—R$^{14}$, —SO$_2$—R$^{15}$, or $R^{16}$ and $R^{17}$ together with the attached N-atom form a five- to seven-membered heterocyclic ring which optionally contains an additional oxygen, sulfur or nitrogen atom in the ring, which groups $R^{16}$ and/or $R^{17}$ or heterocyclic ring forming groups $R^{16}$ and $R^{17}$ are optionally substituted by one or more halogen, hydroxyl, oxo, alkyl, haloalkyl, alkoxy, haloalkoxy, alkylthio, cycloalkyl, aryl, heterocyclyl, aralkyl or heterocyclylalkyl groups, X is —S—, —SO—, or —SO$_2$—, Y is —O—, —S—, —SO—, or —SO$_2$—, Z is hydrogen, halogen, alkyl, alkenyl, alkynyl, cycloalkyl, aryl, heterocyclyl, aralkyl, heterocyclylalkyl or —NR$^{18}$R$^{19}$, $R^{18}$ is hydrogen, alkyl, alkenyl, alkynyl, cycloalkyl, aryl, heterocyclyl, aralkyl, heterocyclylalkyl which group $R^{18}$ is optionally substituted by one or more halogen, hydroxyl, oxo, nitro, cyano, amino, alkyl, haloalkyl, alkoxy, haloalkoxy, alkylthio, cycloalkyl, aryl, heterocyclyl, aralkyl groups and/or by one or more —CO—O—R$^{20}$, —CO—R$^{21}$, —SO—R$^{22}$ and/or —SO$_2$—R$^{23}$ groups, $R^{20}$, $R^{21}$, $R^{22}$ and $R^{23}$ are alkyl, haloalkyl, alkenyl, alkynyl, cycloalkyl, aryl, heterocyclyl, aralkyl or heterocyclylalkyl, which groups $R^{20}$, $R^{21}$, $R^{22}$ and $R^{23}$ are optionally substituted by one or more halogen, hydroxyl, oxo, nitro, cyano, amino, alkyl, haloalkyl, alkoxy, haloalkoxy, alkylthio, cycloalkyl, aryl, heterocyclyl or aralkyl groups, $R^{19}$ is hydrogen, —CO—O—R$^{24}$, —CO—R$^{25}$, —CO—CO—R$^{25}$, —CO—CH$_2$—O—R$^{25}$, —SO—R$^{26}$, —SO$_2$—R$^{27}$, alkyl, alkenyl, alkynyl, cycloalkyl, aryl, heterocyclyl, aralkyl, heterocyclylalkyl which group $R^{19}$ is optionally substituted by one or more halogen, hydroxyl, oxo, nitro, cyano, amino, alkyl, haloalkyl, alkoxy, haloalkoxy, alkylthio, cycloalkyl, aryl, heterocyclyl, aralkyl —NH—CO—R$^{28}$, —NH—R$^{29}$, —NR$^{30}$—CO—R$^{31}$, —O—CO—R$^{32}$, —O—R$^{33}$, —SO$_p$—R$^{34}$, =N—R$^{35}$, =N—NH—R$^{36}$, =N—OR$^{37}$, =N—OH, =N—NH—C(=O)—NH$_2$, =N—NH—C(=O)—NHR$^{31}$, =N—NR$^{38}$—C(=O)—NH$_2$, =N—NH—C(=S)—NH$_2$, =N—NH—C(=S)—NHR$^{31}$, =N—NR$^{38}$—C(=S)—NH$_2$ and/or =N—NH—C(O)—O—R$^{39}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ and $R^{39}$ independently of one another are alkyl, haloalkyl, alkenyl, alkynyl, cycloalkyl, aryl, heterocyclyl, aralkyl or heterocyclylalkyl, which groups $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ and/or $R^{39}$ are optionally substituted by one or more halogen, hydroxyl, oxo, nitro, cyano, amino, alkyl, haloalkyl, alkoxy, haloalkoxy, alkylthio, cycloalkyl, aryl, heterocyclyl or aralkyl groups, or $R^{18}$ and $R^{19}$ together with the attached N-atom form a five- to seven-membered heterocyclic ring which optionally contains an additional oxygen, sulfur or nitrogen atom in the ring and which is optionally substituted by one or more halogen, hydroxyl, oxo, alkyl, haloalkyl, alkoxy, haloalkoxy, alkylthio, cycloalkyl, aryl, heterocyclyl, aralkyl or heterocyclylalkyl groups, or or $R^{18}$ and $R^{19}$ together with the attached N-atom form an imine group —N=CR$^{18a}$R$^{19a}$ or an iminoether group —N=CR$^{18a}$(OR$^{19a}$), $R^{18a}$ is hydrogen, alkyl, cycloalkyl, aryl, heterocyclyl, aralkyl or heterocyclylalkyl, $R^{19a}$ is alkyl, cycloalkyl, aryl, heterocyclyl, aralkyl or heterocyclylalkyl, which groups $R^{18a}$ and $R^{19a}$ independently of one another are optionally substituted by one or more halogen, hydroxyl, oxo, cyano, nitro, alkyl, haloalkyl, alkoxy, haloalkoxy, alkylthio, cycloalkyl, aryl, heterocyclyl, aralkyl or heterocyclylalkyl groups or by amino, which is optionally substituted by alkyl, alkenyl, alkinyl, aryl or heteroaryl groups, and n and p are independently of one another 0, 1, or 2.

In the present specification, including the accompanying claims, the aforementioned groups have the following meanings:

The term "halogen" shall mean fluorine, chlorine, bromine or iodine.

The term "halo" before the name of a radical shall mean that this radical is partially or completely halogenated, that is to say, substituted by F, Cl, Br, or I, in any combination, preferably by F or Cl.

The term "alkyl" shall mean a straight-chain or branched chain saturated aliphatic hydrocarbon group. In general alkyl groups possess one to ten carbon atoms, preferably one to eight carbon atoms. Examples of alkyl groups are methyl, ethyl, propyl, isopropyl, 2-methylpropyl, 1-butyl, 2-butyl, isobutyl, tert-butyl, 2-methylbutyl, 1,1-dimethylpropyl, n-pentyl, n-hexyl, n-heptyl, 2-ethylhexyl or octyl.

The term "($C_1$-$C_6$)-alkyl" is to be understood as meaning an unbranched or branched hydrocarbon radical having one to six carbon atoms.

Alkyl radicals preferably have 1 to 4 carbon atoms.

The term "haloalkyl" shall mean an alkyl group wherein one or more hydrogen atoms are replaced by identical or different halogen atoms, preferably by fluorine and/or chlorine.

Examples for haloalkyl groups are trifluoromethyl, difluoromethyl, monofluoromethyl, 1- or 2-fluoroethyl, 2,2,2-trifluoroethyl, pentafluoroethyl, 1,1,2,2-tetrafluoroethyl, mono-, di- or trichloromethyl, 1-fluoro-2-chloro-ethyl, 1-chloro-2-fluoro-ethyl or 1- or 2-chloroethyl.

Haloalkyl radicals preferably have 1 to 2 carbon atoms.

The term "alkoxy" shall mean a straight-chain or branched chain saturated aliphatic hydrocarbon group which is connected via an oxygen atom to another group. In general alkoxy groups possess one to ten carbon atoms, preferably one to eight carbon atoms. Examples of alkoxy groups are methoxy, ethoxy, propyloxy, isopropyloxy, 1-butyloxy, 2-butyloxy, isobutyloxy, tert-butyloxy, 2-methylbutyloxy, 1,1-dimethylpropyloxy, n-pentyloxy, n-hexyloxy, n-heptyloxy, 2-ethylhexyloxy or octyloxy.

The term "($C_1$-$C_6$)-alkoxy" shall mean an alkoxy group whose carbon chain has the meaning given under the expression "($C_1$-$C_6$)-alkyl".

The term "haloalkoxy" shall mean an alkoxy group wherein one or more hydrogen atoms are replaced by halogen atoms, preferably by fluorine and/or chlorine. Examples for haloalkoxy groups are trifluoromethoxy, difluoromethoxy, monofluoromethoxy, pentafluoroethoxy, 1- or 2-fluoroethoxy, 2,2,2-trifluoroethoxy, chloromethoxy, 2-chloroethoxy or 1,1,2,2-tetrafluoroethoxy.

The term "alkylthio" shall mean a straight-chain or branched chain saturated aliphatic hydrocarbon group which is connected via a sulfur atom to another group. In general alkylthio groups possess one to ten carbon atoms, preferably one to eight carbon atoms. Examples of alkylthio groups are methylthio, ethylthio, propylthio, isopropylthio, 1-butylthio, 2-butylthio, isobutylthio, tert-butylthio, 2-methylbutylthio, 1,1-dimethylpropylthio, n-pentylthio, n-hexylthio, n-heptylthio, 2-ethylhexylthio or octylthio.

The term "alkenyl" shall mean a straight-chain or branched chain unsaturated aliphatic hydrocarbon group possessing one or more non-conjugated double bonds. In general alkenyl groups possess one to ten carbon atoms, preferably one to eight carbon atoms. Examples of alkenyl groups are vinyl, allyl, 2-methyl-2-propenyl, 1- or 2-butenyl, pentenyl, 2-methylpentenyl, hexenyl, heptenyl or octenyl.

The term "($C_2$-$C_6$)-alkenyl" shall mean an unbranched or branched non-cyclic carbon chain having a number of carbon atoms which corresponds to this stated range and which contains at least one double bond which can be located in any position of the respective unsaturated radical.

The term "alkynyl" shall mean a straight-chain or branched chain unsaturated aliphatic hydrocarbon group possessing one or more non-conjugated triple bonds. In general alkynyl groups possess one to ten carbon atoms, preferably one to eight carbon atoms. Examples of alkynyl groups are ethynyl, propargyl, 2-methyl-2-propynyl, 1-methyl-2-propynyl, 2-butynyl, 3-butynyl, pentynyl-, 2-methylpentynyl, hexynyl, heptynyl and octynyl.

The term "cycloalkyl" shall mean a monocyclic and saturated alkyl group having preferably three to seven ring carbon atoms, such as cyclopropyl, cyclobutyl, cyclopentyl, cyclohexyl, cycloheptyl, cyclooctyl or cyclodecyl; or a bicyclic and saturated alkyl group, such as norbornyl or bicyclo[2.2.2] octyl; or condensed and saturated system, such as decahydronaphthalene. Monocyclic cycloalkyl groups with five- or six-membered rings are preferred.

Cycloalkyl groups preferably are optionally substituted by halogen or alkyl.

In compounds of formula I the following examples of preferred substituted alkyl or cycloalkyl radicals are provided:

An example of alkyl substituted by cycloalkyl is cyclopropylmethyl; an example of alkyl substituted by alkoxy, is methoxymethyl —$CH_2OCH_3$; and an example of alkyl substituted by alkylthio is methylthiomethyl —$CH_2SCH_3$.

The term "aryl" shall mean a carbocyclic aromatic group formed from ring-carbon atoms, preferably six to fourteen, especially six to twelve ring carbon atoms. Examples for aryl groups are phenyl, naphthyl or biphenylyl, preferably phenyl.

The term "heterocyclyl" shall mean a cyclic group being fully saturated, partially unsaturated or fully unsaturated which possesses besides at least one ring carbon atom one or more ring heteroatoms selected from the group of oxygen, sulfur and nitrogen. Different ring heteroatoms are possible with the exception of two adjacent ring oxygen atoms. Heterocyclyl groups preferably contain one two or three hetero atoms in the heterocyclic ring, preferably selected from the group consisting of N, O and S (including the oxidized forms of S). Hetero-cyclyl groups are preferably aliphatic heterocyclyl radicals having three to seven ring atoms or heteroaromatic radicals having five to seven ring atoms. Heterocyclic groups can be mono-, bi- or polycyclic heterocyclic systems, preferable heteroaromatic systems in which at least one ring contains one or more hetero atoms.

Examples of heterocyclyl groups are thiophenyl, furyl, pyrrolyl, thiazolyl, oxazolyl, imidazolyl, isothiazolyl, isoxazolyl, pyrazolyl, 1,3,4-oxadiazolyl, 1,3,4-thiadiazolyl, 1,3,4-triazolyl, 1,2,4-oxadiazolyl, 1,2,4-thiadiazolyl, 1,2,4-triazolyl, 1,2,3-triazolyl, 1,2,3,4-tetrazolyl, benzo[b]thiophenyl, benzo[b]furanyl, indolyl, benzo[c]thiophenyl, benzo[c]furanyl, isoindolyl, benzoxazolyl, benzothiazolyl, benzimidazolyl, benzisoxazolyl, benzisothiazolyl, benzopyrazolyl, benzothiadiazolyl, benzotriazolyl, dibenzofuranyl, dibenzothiophenyl, carbazolyl, pyridyl, pyrazinyl, pyrimidinyl, pyridazinyl, 1,3,5-triazinyl, 1,2,4-triazinyl, 1,2,4,5-tetrazinyl, quinolinyl, isoquinolinyl, chinoxalinyl, chinazolinyl, cinnolinyl, 1,8-naphthyridinyl, 1,5-naphthyridinyl, 1,6-naphthyridinyl, 1,7-naphthyridinyl, phthalazinyl, pyridopyrimidinyl, purinyl, pteridinyl, 4H-quinolizinyl, piperidinyl, pyrrolidinyl, oxazolinyl, tetrahydrofuranyl, tetrahydropyranyl, isoxazolidinyl, thiazolidinyl, thienyl, oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl.

The term "heteroaromatic group" is a subgroup of the term "heterocyclyl group" and encompasses the in the above list mentioned fully unsaturated aromatic heterocyclic compounds.

Heterocyclyl groups may be unsubstituted or substituted, preferably by one or more radicals, very preferably by one to three radicals selected from the group consisting of halogen, alkoxy, haloalkoxy, alkylthio, hydroxyl, amino, nitro, carboxyl, cyano, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl, alkyl and haloalkyl, and additionally also oxo. The oxo group can also be present at those hetero ring atoms where various oxidation numbers are possible, for example in the case of N and S.

Heterocyclyl shall preferably mean an unsaturated, partially saturated or aromatic ring system with three to six ring carbon atoms and one to four ring hetero atoms selected from the group oxygen, sulfur and nitrogen or their combinations.

Two groups together with an attached N-atom may form a five- to seven-membered heterocyclic ring which optionally contains an additional oxygen, sulfur or nitrogen atom in the ring. Examples of nitrogen-containing rings formed are given in the list of heterocyclyl groups.

Furthermore, two groups $R^2$ and $R^3$ together with the attached S- and optionally O-atoms may form a five- to nine-membered, preferably a five- to eight-membered heterocyclic ring which optionally contains additional heteroatoms, preferably oxygen, sulfur or nitrogen atoms, in the ring. The five- to eight-membered heterocyclic ring may form part of a higher condensed ring system the heterocyclic ring system in such case contains condensed at two adjacent C-atoms of the heterocyclic ring system additional carbocyclic and/or heterocyclic saturated and/or unsaturated ring systems. Examples of these heterocyclic groups are given in the list of heterocyclyl groups.

The term "aralkyl" shall mean an aryl group which is connected via an alkylene group to another group. The alkylene portion is a saturated straight-chain or branched-chain hydrocarbon portion possessing in general one to six carbon atoms. Preferred aralkyl group is benzyl.

The term "heterocyclylalkyl" shall mean a heterocyclyl group which is connected via an alkylene group to another group. The alkylene portion is a saturated straight-chain or branched-chain hydrocarbon portion possessing in general one to six carbon atoms.

Preferred are compounds of formula I wherein W is $=N—$, $=CR^7—$ or $=C(NR^8R^9)—$.

Very preferred W is $=C(halogen)-$, $=C(NH_2)—$ or $=N—$, more preferred $=N—$ and $=C(halogen)-$ and most preferred W is $=C(halogen)-$.

Preferred are compounds of formula I, wherein $R^7$ is chlorine or fluorine.

Preferred are compounds of formula I, wherein $R^1$ is cyano, halogen, haloalkyl or $—CS—NH_2$.

Preferred are compounds of formula I, wherein $R^2$ is alkyl or haloalkyl.

Preferred are compounds of formula I, wherein $R^3$ is alkyl or haloalkyl.

Preferred are compounds of formula I, wherein $R^2$ and $R^3$ are linked together to form a five to eight membered heterocyclic saturated or unsaturated ring system with two sulfur ring atoms or with one sulfur and one oxygen ring atom or wherein $R^2$ and $R^3$ are linked together to form a condensed ring system possessing a five to eight membered heterocyclic saturated or unsaturated ring system with two sulfur ring atoms or with one sulfur and one oxygen ring atom to which at least one other carbocyclic and/or heterocyclic ring system is fused at two adjacent C-atoms of the five to eight membered heterocyclic saturated or unsaturated ring system.

The sulfur ring atom(s) can be oxidized and can carry one or two oxygen atoms.

Preferred are compounds of formula I, wherein $R^4$ is hydrogen, alkyl or haloalkyl.

$R^4$ is very preferably hydrogen, $(C_1-C_3)$-alkyl or $(C_1-C_3)$-haloalkyl.

Preferred are compounds of formula I, wherein $R^5$ is halogen, haloalkyl, haloalkoxy or $—SF_5$.

$R^5$ is very preferably halogen, $(C_1-C_3)$-haloalkoxy, $(C_1-C_3)$-haloalkyl or $—SF_5$.

Preferred are compounds of formula I, wherein $R^6$ is hydrogen, halogen, nitro or $—NR^{16}R^{17}$.

Preferred are compounds of formula I, wherein X and Y are each $—S—$ or $—SO—$ or $—SO_2—$ or wherein Y is $—O—$ and X is $—S—$, $—SO—$ or $—SO_2—$.

Preferred are compounds of formula I, wherein Y is $—S—$.

Preferred are compounds of formula I, wherein Z is hydrogen, halogen, alkylthio or $—NR^{18}R^{19}$.

Very preferred are compounds of formula I, wherein $R^1$ is $(C_1-C_3)$-haloalkyl, halogen, cyano, $—CS—NH_2$ or $C(=NR^{10})S(O)_nR^{11}$;

$R^2$ and $R^3$ independently of one another are $(C_1-C_3)$-alkyl, $(C_1-C_3)$-haloalkyl, or $R^2$ and $R^3$ are linked together to form a five to eight membered heterocyclic saturated or unsaturated ring system with at least one ring heteroatom being sulfur, at least another ring heteroatom being sulfur or oxygen and optionally a third ring heteroatom being selected from oxygen, nitrogen or sulfur, or wherein $R^2$ and $R^3$ are linked together to form a condensed ring system possessing a five to eight membered heterocyclic saturated or unsaturated ring system with at least one ring heteroatom being sulfur, at least another ring heteroatom being sulfur or oxygen and optionally a third ring heteroatom being selected from oxygen, nitrogen or sulfur, to which ring system at least one other carbocyclic and/or heterocyclic ring system is fused at two adjacent C-atoms of the five to eight membered heterocyclic saturated or unsaturated ring system, $R^4$ is hydrogen, $(C_1-C_3)$-alkyl or $(C_1-C_3)$-haloalkyl, $R^5$ is $—CF_3$, $—OCF_3$, $—SF_5$ or halogen, $R^6$ is hydrogen, halogen, $—NO_2$, or $—NR^{16}R^{17}$, W is $=C(halogen)-$, $=C(NR^8R^9)—$ or $=N—$, X is $—S—$, $—SO—$ or $—SO_2—$, Y is $—O—$, $—S—$, $—SO—$ or $—SO_2—$, Z is hydrogen, halogen, alkylthio or $NR^{18}R^{19}$, $R^{10}$ is hydrogen, $(C_1-C_6)$-alkyl, $(C_1-C_6)$-haloalkyl, $(C_2-C_6)$-alkenyl, $(C_2-C_6)$-alkynyl, $—(CH_2)_q—R^{40}$, $—CO—R^{43}$, $—CO_2—(C_1-C_6)$-alkyl, $—S(O)_p—R^{41}$ or $—S(O)_p—R^{40}$, $R^{11}$ is $(C_1-C_6)$-alkyl or $—CH_2—R^{40}$, $R^{18}$ is hydrogen, $(C_2-C_6)$-alkenyl, $(C_2-C_6)$-alkynyl, $R^{40}$, $R^{41}$, $(C_1-C_6)$-cycloalkyl or $(C_1-C_4)$-alkyl which last mentioned group is unsubstituted or substituted by one or more radicals selected from the group consisting of halogen, $(C_1-C_4)$-alkoxy, $—S(O)_m—R^{42}$, $R^{40}$, $(C_3-C_6)$-cycloalkyl, $—CO_2—(CH_2)_q—R^{40}$, $—CO_2—(CH_2)_q—R^{41}$ and $—CO_2—R^{42}$, $R^{19}$ is hydrogen, $—CO_2R^{44}$, $—COCOR^{45}$, $—SO_2R^{43}$, $—COR^{43}$ or $—COCH_2OR^{43}$, $(C_1-C_4)$-alkyl or $(C_1-C_4)$-haloalkyl which alkyl or haloalkyl groups are unsubstituted or substituted by a radical selected from the group consisting of $—NHCOR^{43}$, $—NHR^{43}$, $—NR^{43}COR^{43}$, $—OCOR^{43}$, $—OR^{40}$, $—OR^{41}$, $—S(O)_p(CH_2)_qR^{40}$, $—S(O)_p(CH_2)_qR^{41}$, $=N—R^{43}$, $=NNHR^{43}$, $=NOR^{43}$, $=NOH$, $=NNHC(=O)R^{43}$, $=NNHC(=O)NH_2$, $=NNHC(=O)NHR^{31}$, $=NNR^{43}C(=O)NH_2$, $—NNHC(=S)R^{43}$, $=NNHC(=S)NH_2$, $=NNHC(=S)NHR^{31}$, $=NNR^{43}C(=S)NH_2$, $=NNHC(=O)O(CH_2)_qR^{44}$, $(C_1-C_4)$-alkoxy and $—S(O)_mR^{42}$, wherein two $(C_1-C_4)$-alkoxy or $—S(O)_mR^{42}$ radicals may be attached to the same carbon atom to form an acetal, thioacetal or hemithioacetal group or a cyclic acetal, thioacetal or hemithioacetal which contains 5 or 6 ring atoms; or $R^{18}$ and $R^{19}$ together with the 5-nitrogen can also form an $C_1-C_3$ alkyl iminoether group, $R^{40}$ is phenyl unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $—CN$, $—NO_2$, $S(O)_p—R^{42}$ and $—NR^{46}R^{47}$, $R^{41}$ is heteroaryl unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, —CN, —NO$_2$, —S(O)$_p$—R$^{42}$, —NR$^{46}$R$^{47}$, —OH and oxo, $R^{42}$ is $(C_1-C_4)$-alkyl or $(C_1-C_4)$-haloalkyl, $R^{43}$ is $(C_1-C_4)$-alkyl, $(C_1-C_4)$-haloalkyl, $(C_3-C_6)$-cycloalkyl-$(C_1-C_3)$-alkyl or —(CH$_2$)$_q$—R$^{40}$, $R^{44}$ is $R^{40}$, $(C_3-C_4)$-alkenyl, $(C_3-C_4)$-alkynyl or $(C_1-C_4)$-alkyl which last mentioned group is unsubstituted or substituted by one or more radicals selected from the group consisting of halogen, $(C_1-C_4)$-alkoxy, $(C_1-C_4)$-haloalkoxy, $R^{40}$, —S(O)$_m$—R$^{40}$ and $(C_3-C_6)$-cycloalkyl, $R^{45}$ is —OR$^{44}$ or —NR$^{46}$R$^{47}$, $R^{16}$, $R^{17}$, $R^{46}$ and $R^{47}$ independently of one another are hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_3-C_6)$-cycloalkyl, $(C_3-C_6)$-cycloalkyl-$(C_1-C_4)$-alkyl, $R^{44}$, —(CH$_2$)$_q$—R$^{40}$; or $R^{16}$ and $R^{17}$ or $R^{46}$ and $R^{47}$ together with the attached N atom form a five- or six-membered saturated or unsaturated ring which optionally contains an additional hetero atom in the ring which is selected from O, S and N, the ring being unsubstituted or substituted by one or more radicals selected from the group consisting of halogen, $(C_1-C_4)$-alkyl, $(C_1-C_4)$-haloalkyl and oxo, m, n and p are each independently 0, 1, or 2, q is 0 or 1, and each heteroaryl in the above-mentioned radicals is independently a heteroaromatic radical having 3 to 7 ring atoms and 1, 2 or 3 hetero atoms in the ring selected from the group consisting of N, O and S (including the oxidized forms);

or a pesticidally acceptable salt thereof.

In the following preferred definitions it is generally to be understood that where symbols are not specifically defined they are to be as previously defined in the description.

A preferred class of compounds of formula I are those in which:

$R^1$ is CN or $(C_1-C_3)$-haloalkyl, $R^2$, $R^3$, X and Y are linked together to form 1,3-dithiolane or 1,3-dithiane ring systems, $R^4$ is hydrogen, W is =C(halogen)- or =N—, and the other radicals are as defined above.

Another preferred class of compounds of formula I are those in which:

$R^1$ is CN, $R^4$ is $(C_1-C_3)$-alkyl or $(C_1-C_3)$-haloalkyl,

W is =C(halogen)- or =C(NR$^8$R$^9$)—, and the other radicals are as defined above.

Another preferred class of compounds of formula I are those in which:

$R^1$ is CN, $R^2$, $R^3$, X and Y are linked together to form 1,3-dithiolane or 1,3-dithiane ring systems, $R^4$ is hydrogen, Z is —NR$^8$R$^9$ W is =C(halogen)- or =N—, and the other radicals are as defined above.

Another preferred class of compounds of formula I are those wherein:

$R^1$ is CN, $R^2$, $R^3$, X and Y are linked together to form 1,3-dithiolane or 1,3-dithiane ring systems, $R^4$ is hydrogen, Z is —NR$^{18}$R$^{19}$, W is =C(halogen)- or =N—, $R^5$ is —CF$_3$, —OCF$_3$ or —SF$_5$, $R^6$ is halogen or NR$^{16}$R$^{17}$, and the other radicals are as defined above.

A further preferred class of compounds of formula I are those wherein:

$R^1$ is CN, $R^2$, $R^3$, X and Y are linked together to form 1,3-dithiolane or 1,3-dithiane ring systems, $R^4$ is hydrogen, Z is —NR$^{18}$R$^{19}$, $R^{18}$ is hydrogen, $(C_2-C_6)$-alkenyl, $(C_1-C_4)$-alkyl which last mentioned group is unsubstituted or substituted by one or more radicals selected from the group consisting of halogen, $(C_1-C_4)$-alkoxy, —S(O)$_m$R$^{42}$, $R^{40}$, —CO$_2$—(CH$_2$)$_q$—R$^{40}$, —CO$_2$(CH$_2$)$_q$R$^{41}$ and —CO$_2$R$^{42}$, $R^{19}$ is hydrogen, —CO$_2$R$^{44}$, —COCOR$^{45}$, —SO$_2$R$^{43}$, —COR$^{43}$, or —COCH$_2$OR$^{43}$, $(C_1-C_4)$-alkyl or $(C_1-C_4)$-haloalkyl which alkyl or haloalkyl groups are unsubstituted or substituted by a radical selected from the group consisting of —NHCOR$^{43}$, —NHR$^{43}$, —NR$^{43}$COR$^{43}$, —OCOR$^{43}$, —OR$^{40}$, —OR$^{41}$, —S(O)$_p$(CH$_2$)$_q$R$^{41}$, —S(O)$_p$(CH$_2$)$_q$R$^{41}$, =N—R$^{43}$, =NNHR$^{43}$, =NOR$^{43}$, =NOH, =NNHC(=O)R$^{43}$, =NNHC(=O)NH$_2$, =NNHC(=O)NHR$^{31}$, =NNR$^{43}$C(=O)NH$_2$, —NNHC(=S)R$^{43}$, =NNHC(=S)NH$_2$, =NNHC(=S)NHR$^{31}$, —NNR$^{43}$C(=S)NH$_2$, =NNHC(=O)O(CH$_2$)$_q$R$^{44}$, $(C_1-C_4)$-alkoxy and —S(O)$_m$R$^{42}$, wherein two $(C_1-C_4)$-alkoxy or —S(O)$_m$R$^{42}$ radicals may be attached to the same carbon atom to form an acetal, thioacetal or hemithioacetal group or a cyclic acetal, thioacetal or hemithioacetal which contains 5 or 6 ring atoms, W is =C(halogen)- or =N—, $R^5$ is —CF$_3$, —OCF$_3$, or —SF$_5$, $R^6$ is halogen or —NR$^{16}$R$^{17}$, and the other radicals are as defined above.

A further preferred class of compounds of formula I are those wherein:

$R^1$ is CN, $R^2$, $R^3$, X and Y are linked together to form 1,3-dithiolane or 1,3-dithiane ring systems, $R^4$ is hydrogen, Z is —NR$^{18}$R$^{19}$, $R^{18}$ is hydrogen, $(C_2-C_6)$-alkenyl, $(C_1-C_4)$-alkyl which last mentioned group is unsubstituted or substituted by one or more radicals selected from the group consisting of halogen, $(C_1-C_4)$-alkoxy, —S(O)$_m$R$^{42}$, $R^{40}$, —CO$_2$(CH$_2$)$_q$R$^{40}$, —CO$_2$(CH$_2$)$_q$R$^{41}$ and —CO$_2$R$^{42}$, $R^{19}$ is hydrogen, —CO$_2$R$^{44}$, —COCOR$^{45}$, —SO$_2$R$^{43}$, —COR$^{43}$ or —COCH$_2$OR$^{43}$, $(C_1-C_4)$-alkyl or $(C_1-C_4)$-haloalkyl which alkyl or haloalkyl groups are unsubstituted or substituted by a radical selected from the group consisting of —S(O)$_m$R$^{42}$, wherein two $(C_1-C_4)$-alkoxy or —S(O)$_m$R$^{42}$ radicals may be attached to the same carbon atom to form an acetal, thioacetal or hemithioacetal group or a cyclic acetal, thioacetal or hemithioacetal which contains 5 or 6 ring atoms, W is =C(halogen)-, $R^5$ is —CF$_3$, $R^6$ is halogen, and the other radicals are as defined above.

Compounds of formula I possess valuable pesticidal properties.

The invention also encompasses any stereoisomer, enantiomer or geometric isomer, and mixtures thereof.

By the term "pesticidally acceptable salts" is meant salts the anions of which are known and accepted in the art for the formation of salts for pesticidal use.

Suitable acid addition salts, e.g. formed by compounds of formula I containing an amino group, include salts with inorganic acids, for example hydrochlorides, sulphates, phosphates and nitrates and salts with organic acids for example acetic acid.

The term pests means arthropod pests (including insects and arachnids), and helminths (including nematodes).

The compounds of general formula I can be prepared by the application or adaptation of known methods (i.e. methods heretofore used or described in the chemical literature.

In the following description of processes when symbols appearing in formulae are not specifically defined, it is understood that they are "as defined above" in accordance with the first definition of each symbol in the specification.

According to a further feature of the invention compounds of formula I wherein $R^1$, $R^2$, $R^3$, $R^4$, $R^5$, $R^6$, Z and W are as defined above, may be prepared by the reaction of a corresponding compound of formula II described in WO-A-98/04530:

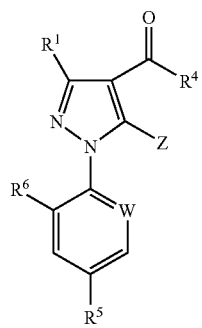

(II)

wherein the various values are as defined above, with a compound of formula III $R^2$—XH or $R^3$—YH or HX—$R^2$—$R^3$—YH     (III)

in the presence of N-bromosuccinmide in an organic solvent, for example in dichloromethane. Alternatively, the use of borontrifluoride-acetic acid as the catalyst during the reaction of II and III in 1,2-dichloroethane at room temperature or at elevated temperature also provided the conversion.

According to a feature of the invention compounds of formula I, wherein $R^{19}$ is alkyl or haloalkyl which groups are substituted by a radical selected from the group consisting of —N—$R^{43}$, =NO$R^{43}$, =NOH, =NNHC(=O)$R^{43}$, =NNHC(=O)NH$_2$, =NNHC(=O)NHR$^{31}$, —NNR$^{43}$C(=O)NH$_2$, =NNHC(=S)R$^{43}$, =NNHC(=S)NH$_2$, =NNHC(=S)NHR$^{31}$, =NNR$^{43}$C(=S)NH$_2$, =NNHC(=O)O(CH$_2$)$_q$R$^{44}$, $R^1$, $R^2$, $R^3$, $R^4$, $R^5$, $R^6$, W, n, q and p are as defined above, may be prepared by the reaction of a corresponding compound of formula I in which the alkyl carbon atom bearing the relevant radical is replaced by a carbon atom substituted by a carbonyl group or by an acetal derivative thereof, preferably a (C$_1$-C$_4$)-alkyl acetal derivative, with a compound of formula (IV), (V), (VI), (VII), (VIII), (IX), (X), (XI), (XII), (XIII), (XIV), (XV) or (XVI)

NH$_2$—R$^{43}$     (IV)

NH$_2$NHR$^{43}$     (V)

NH$_2$OR$^{43}$     (VI)

NH$_2$OH     (VII)

NH$_2$NHC(=O)R$^{43}$     (VIII)

NH$_2$NHC(=O)NH$_2$     (IX)

NH$_2$NR$^{43}$C(=O)NH$_2$     (X)

NH$_2$NHC(=S)R$^{43}$     (XI)

NH$_2$NHC(=S)NH$_2$     (XII)

NH$_2$NR$^{43}$C(=S)NH$_2$     (XIII)

NH$_2$NHC(=O)O(CH$_2$)$_q$R$^{44}$     (XIV)

NH$_2$NHC(=O)NHR$^{31}$     (XV)

NH$_2$NHC(=S)NHR$^{31}$     (XVI)

wherein the various values are as defined above, or an acid salt thereof, such as the hydro chloride salt.

When the compound of formula I used in the reaction contains a carbon atom substituted by a carbonyl group, the reaction is generally performed in the presence of a base, in a solvent such as an alcohol or an ether, for example methanol, or dioxan, at a temperature of from 0° C. to the reflux temperature of the solvent. The base is generally at alkali metal carbonate such as sodium carbonate or potassium carbonate, or an organic base such as a tertiary amine, for example triethylamine or ethyldiisopropylamine, or pyridine, or 1,8 diazabicyclo[5.4.0]undec-7 en (DBU).

When the compound of formula I used in the reaction contains a carbon atom substituted by at acetal moiety, the reaction is generally performed in the presence of a strong acid such as a mineral acid, for example hydrochloric acid, in a solvent such as an alcohol or an ether, for example methanol or dioxan, at a temperature of from 0° C. to the reflux temperature of the solvent.

According to a feature of the invention compounds of formula I, wherein $R^1$ of is —CSNH$_2$, and the other values are as defined above, may be prepared by the reaction of the corresponding compound of formula I, wherein $R^1$ is CN, with alkali or alkaline earth metal hydro sulphides, such as sodium or lithium, potassium, calcium preferably hydro sulphides, in at inert solvent, for example N,N-dimethylformamide, pyridine, dioxan, tetrahydrofuran, sulfolane, dimethyl sulfoxide, methanol or ethanol at a temperature from –35° C. to 50° C. preferably 0° C. to 30° C. Optionally the hydrosulphides may be generated in situ by treatment with H$_2$S in the presence of at organic base, such as a metal alkoxide or trialkylamine or an inorganic base, such as metal alkaline or alkaline earth hydroxide or a carbonate, such as sodium carbonate or potassium or ammonium carbonate. The use of a metal complexing agent, such as a crown ether, can be of benefit in accelerating the reaction.

The reaction of hydrosulphide salt with the compound of formula I can therefore be conducted in a two-phase water/organic solvent system using a phase transfer catalyst such as a crown ether or a tetraalkylammonium salt such as benzyltrimethylammonium chloride or as tetra-n-butylammonium bromide. Organic solvents suitable for use in a two-phase system with water include benzene, toluene, dichloromethane, 1-chlorobutane and methyl tertiary-butyl ether.

Alternatively compounds of formula I, wherein $R^1$ is —CS—NH$_2$ may be prepared from the corresponding compound of formula I, wherein $R^1$ is —CN by treatment with the reagent Ph$_2$PS$_2$ as described in Tet. Lett., 24 (20), 2059 (1983).

According to a feature of the invention compounds of formula I, wherein $R^1$ is —CS—NH$_2$, and the other values are as defined above may be prepared by the reaction of the corresponding compound of formula I, wherein $R^1$ is —CN, with a bis(trialkylsilyl)sulfide, preferably bis(trimethylsilyl)sulfide, in the presence of a base generally an alkali metal alkoxide such as methoxide sodium, in a solvent such as N,N-dimethylformamide, at a temperature of from 0° C. to 60° C. The procedure is generally described by Lin, Ku of and Shiao in Synthesis 1219 (1992).

According to a feature of the invention compounds of formula I, wherein n, q or p are 1 or 2 and $R^1$, $R^2$, $R^3$, $R^4$, $R^5$, $R^6$, Z and W are as defined above, may be prepared by oxidising a corresponding compound in which n, q or p are 0 or 1. The oxidation is generally performed using a peracid, such as 3-chloroperbenzoic acid in a solvent, such as dichloromethane or in 1,2-dichloroethane, at a temperature of from 0° C. to the reflux temperature of the solvent.

Intermediates of formula II may be prepared as described in WO-A-98/04530.

Collections of compounds of the formula I which can be synthesized by the above mentioned process may therefore be prepared in a parallel manner, and this may be effected manually or in a semiautomated or fully automated manner. In this case, it is possible, for example, to automate the procedure of the reaction, work-up or purification of the products or of the intermediates. In total, this is to be understood ace meaning a procedure as is described, for example, by S. H. Dewitt in "Annual report in Combinatorial Chemistry of and Molecular Diversity: Automated Synthesis", Volume 1, publishing house Escom 1997, pages 69 to 77.

A series of commercially available apparatuses ace are offered by, for example, Stem Corporation, Woodrolfe Road, Tollesbury, Essex, CM9 8SE, England of or H+P laboratory technology Ltd., Bruckmannring 28, 85764 Oberschleiβ-heim, Germany of or Radleys, Shirehill, Saffron Walden, Essex, England, May be used for the parallel procedure of the reaction and work-up.

For the parallel purification of compounds of the formula I or of intermediates obtained during the preparation, use may of be made, inter alia, of chromatography apparatuses, for example those by ISCO, Inc., 4700 superiors Street, Lincoln, Nebr. 68504, USA.

The apparatuses mentioned lead to a modular procedure in which the individual process steps are automated, but manual operation must be performed between the process steps. This can be prevented by employing semi-integrated or fully integrated automation of system of where the automation modules in question are operated by, for example, robots. Look automation of system of can be obtained, for example, from Zymark Corporation, Zymark Center, of Hopkinton, Mass. 01748, for USA.

In addition to what has been described here, compounds of the formula I may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A., Bunin in "The Combinatorial index", Academic Press, 1998.

The use of solid-phase-supported synthesis methods permits a series of protocols which are known from the literature and which, in does gymnastics, can be performed manually or in at automated manner. For example, the "tea-bag method" (Houghten) U.S. Pat. No. 4,631,211; Houghten et al., Proc. Natl. Acad. Sci, 1985, 82, 5131-5135, in which products by IRORI, 11149 North Torrey Pines Road, La Jolla Calif. 92037 USA, are employed, May be semiautomated. The automation of solid-phase-supported, parallel syntheses is performed successfully, for example, by apparatuses by Argonaut Technologies, Inc., 887 Industrial Road, San Carlos, Calif. 94070, USA or MultiSynTech Ltd., Wullener field 4, 58454 Witten Germany.

The preparation of the processes described herein yields compounds of the formula I in the form of substance collections which are termed libraries. The present invention also relates to libraries which comprise at least of two compounds of the formula I.

Compounds of formula III, IV, V, VI, VII, VIII, IX, X, XI, XII, XIII, XIV, XV and XVI are known or may be prepared by known methods.

The following non-limiting Examples illustrate the preparation of the compounds of formula I.

CHEMICAL EXAMPLES

NMR spectra were run in deuterochloroform unless stated otherwise.

In the Examples which follow, quantities, therefore percentages, are weight based, unless stated otherwise. Ratios of solvents are volume based.

Example 1

5-amino-1-[2,6-dichloro-4-(trifluoromethyl)phenyl]-4-(1,3-dithiolan-2-yl)-1H-pyrazole-3-carbonitrile (compound 1-1)

To the solution of 5-amino-1-[2,6-dichloro-4-(trifluoromethyl)phenyl]-4-formyl-1H-pyrazole-3-carbonitrile (5.00 g, 13.7 mmol) in dichloromethane (100 mL) at room temperature was added N-bromosuccinimide (0.74 g, 4.1 mmol) followed by 1,2-ethanedithiol (1.98 g, 20.6 mmol). The resulting mixture was stirred at room temperature for 3.7 hr. It was then worked up by adding 2 N sodium hydroxide. The layers were separated and the organic layer was washed with brine and then dried (sodium sulfate). It was then concentrated to afford a light beige solid (7.0 g). 19F-NMR: −63.791.

Example 2

5-amino-1-[2,6-dichloro-4-(trifluoromethyl)phenyl]-4-(1,3-dithiolan-2-yl)-1H-pyrazole-3-carbonitrile-ethoxyethylene (1:1) (compound 1-5)

To 5-amino-1-[2,6-dichloro-4-(trifluoromethyl)phenyl]-4-(1,3-dithiolan-2-yl)-1H-pyrazole-3-carbonitrile (0.30 g, 0.71 mmol) in triethyl orthoformate (4.45 g, 29.70 mmol) was added p-toluenesulfonic acid (18 mg). The resulting mixture was heated up to 100 C for 1.5 hr. It was then cooled and then concentrated. The resulting viscous liquid was diluted with dichloromethane (20 mL). The organic layer was washed with saturated sodium bicarbonate, brine, and then dried over sodium sulfate to provide, upon concentration, a yellow oil (0.35 g, 0.72 mmol); 19F-NMR: −63.698.

Example 3

1-[2,6-dichloro-4-(trifluoromethyl)phenyl]-4-(1,3-dithiolan-2-yl)-5-(methylamino)-1H-pyrazole-3-carbonitrile (compound 1-6)

To the solution of 5-amino-1-[2,6-dichloro-4-(trifluoromethyl)phenyl]-4-(1,3-dithiolan-2-yl)-1H-pyrazole-3-carbonitrile-ethoxyethylene (1:1) (0.30 g, 0.6 mmol) in ethanol (40 mL) at 5 C was added sodium borohydride (74 mg, 1.9 mmol). The resulting mixture was stirred at room temperature for five hrs and then diluted with water and ethyl acetate. The layers were separated and the organic layer was washed with saturated sodium chloride, dried ($Na_2SO_4$), concentrated to afford a yellowish oil (0.27 g, 0.6 mmol); 19-F-NMR: −63.704.

Example 4

1-[2,6-dichloro-4-(trifluoromethyl)phenyl]-5-(methylamino)-4-[1-oxido-1,3-dithiolan-2-yl]-1H-pyrazole-3-carbonitrile (compound 1-7 & 1-8)

To the solution of 1-[2,6-dichloro-4-(trifluoromethyl)phenyl]-4-(1,3-dithiolan-2-yl)-5-(methylamino)-1H-pyrazole-3-carbonitrile (0.16 g, 0.4 mmol) in 1,2-dichloroethane at 0-5 C was added m-chloroperbenzoic acid (90 mg, 70%, 0.4 mmol) and stirred at that temperature range for one hour. The reaction was worked up by the addition of 2 N sodium hydroxide (10 mL) and ethyl acetate (25 mL). After stirring at room temperature for 5 minutes, The layers were separated and the organic layer was washed with water and saturated sodium chloride. It was then dried ($Na_2SO_4$) and concentrated to afford a yellow semi-solid. Upon chromatographic purification on silica gel column eluting with heptane:ethyl acetate (1:1 to 1:3), two products as white solid were isolated as the sulfoxides (16.1 mg, 70.8 mg, combined yield 47%). 19F-NMR: −63.693 and the other −63.682.

Example 5

1-[2,6-dichloro-4-(trifluoromethyl)phenyl]-4-(1,3-dithiolan-2-yl)-5-(methylamino)-1H-pyrazole-3-carbothioamide (compound 2-6)

To 1,1,1,3,3,3-hexamethyldisilathiane (0.157 g, 0.9 mmol) in dimethylformamide (4 mL) was added sodium methoxide (0.049 g, 0.9 mmol) and the resulting mixture was sonicated to provide a homogeneous blue colored solution. This resulting solution was added to the solution of 1-[2,6-dichloro-4-(trifluoromethyl)phenyl]-4-(1,3-dithiolan-2-yl)-5-(methylamino)-1H-pyrazole-3-carbonitrile (0.08 g, 0.2 mmol) in dimethylformamide (5 mL) at room temperature under nitrogen. This mixture was stirred at room temperature for one and half hour. It was then diluted with ether (30 mL) and water (30 mL). The layers were separated and the aqueous layer was extracted with ether. The ethereal layers were combined and washed twice with water (2×20 mL), dried ($Na_2SO_4$), and concentrated to provide a yellow solid. Upon chromatographic purification via silica gel eluting with heptane:ethyl acetate (4:1 to 2:1), a yellow solid (0.048 g, 55%) was obtained. 19F-NMR: −63.634.

Example 6

5-amino-1-[2,6-dichloro-4-(trifluoromethyl)phenyl]-4-(1,3-dithian-2-yl)-1H-pyrazole-3-carbonitrile (compound 1-93)

To the solution of 5-amino-1-[2,6-dichloro-4-(trifluoromethyl)phenyl]-4-formyl-1H-pyrazole-3-carbonitrile (0.5 g, 1.4 mmol) in dichloromethane (10 mL) was added N-bromosuccinimide (0.075 g, 0.2 mmol) followed by the addition of 1,3-dimercaptopropane (0.19 g, 1.8 mmol). The resulting solution was stirred at room temperature for eight hours. It was then worked-up by the addition of 2 N sodium hydroxide. The layers were separated and the organic layer was dried ($Na_2SO_4$) and concentrated. The resulting solid was further purified via silica gel column eluting with heptane:ethyl acetate (1:1) to afford a white solid (0.2 g, 33%). 19F-NMR: −64.231.

Example 7

5-amino-4-[bis(ethylthio)methyl]-1-[2,6-dichloro-4-(trifluoromethyl)phenyl]-1H-pyrazole-3-carbonitrile (compound 1-61)

To the solution of 5-amino-1-[2,6-dichloro-4-(trifluoromethyl)phenyl]-4-formyl-1H-pyrazole-3-carbonitrile (0.5 g, 1.4 mmol) and N-bromosuccinimide (0.075 g, 0.2 mmol) in methylene chloride (10 mL) was added ethanethiol (0.26 g, 4.2 mmol). The resulting solution was heated at reflux for eight hours. It was then cooled and was added 2 N sodium hydroxide. The layers were separated and the organic layer was dried ($Na_2SO_4$) and concentrated. Upon chromatographic purification via silica gel column eluting with heptane:ethyl acetate (1:1), a yellow solid (0.35 g, 55%) was obtained. 19F-NMR: −64.226.

The following preferred compounds shown in Tables 1 to 3 also form part of the present invention, and were or may be prepared in accordance with, or analogously to, the abovementioned Examples 1 to 7 or the above-described general methods.

In the Tables Me means methyl, Et means ethyl, Pr means n-propyl, cPr means cyclopropyl, OMe means methoxy, OEt means ethoxy, Ph means phenyl.

19F-NMR spectra shift values are given in ppm.

Compound numbers are given for reference purposes only.

TABLE I

Compounds of formula I in which the substituents have the following meanings:
$R_1$ is —CN, $R^5$ is —$CF_3$, $R^6$ is —Cl, W is =C(Cl)—

| Cpd No. | $R^2$ & $R^3$ | $R^4$ | X | Y | Z | Mp or $^{19}$F-NMR |
|---|---|---|---|---|---|---|
| 1-1 | —CH2CH2— | H | S | S | NH2 | −63.791 |
| 1-2 | —CH2CH2— | H | S | SO | NH2 | −63.806 |
| 1-3 | —CH2CH2— | H** | S | SO | NH2 | −63.808 |
| 1-4 | —CH2CH2— | H | SO | SO | NH2 | −63.806, −63.833 |
| 1-5 | —CH2CH2— | H | S | S | N=CHOEt | −63.698 |
| 1-6 | —CH2CH2— | H | S | S | NHMe | −63.704 |
| 1-7 | —CH2CH2— | H | S | SO | NHMe | −63.693 |
| 1-8 | —CH2CH2— | H** | S | SO | NHMe | −63.682 |
| 1-9 | —CH2CH2— | H | S | S | N=CMe(OEt) | −63.720 |
| 1-10 | —CH2CH2— | H | S | S | NHEt | −63.682 |

TABLE I-continued

Compounds of formula I in which the substituents have the following meanings:
R₁ is —CN, R⁵ is —CF₃, R⁶ is —Cl, W is =C(Cl)—

| Cpd No. | R² & R³ | R⁴ | X | Y | Z | Mp or ¹⁹F-NMR |
|---|---|---|---|---|---|---|
| 1-11 | —CH2CH2— | H | S | S | NHC(OEt)2Me | −63.666 |
| 1-12 | —CH(Me)CH(Me)— | H | S | S | NH2 | −63.785 |
| 1-13 | —CH2CH2— | H | S | S | NHiPr | −63.671 |
| 1-14 | —CH(Me)CH(Me)— | H | S | SO | NH2 | −63.796, −63.806 |
| 1-15 | —CH(Me)CH(Me)— | H** | S | SO | NH2 | −63.779, −63.796 |
| 1-16 | —CH2CH2— | H | SO | S | NHiPr | −63.655 |
| 1-17 | —CH2CHMe— | H | S | S | NH2 | −63.790 |
| 1-18 | —CH2CHMe— | H | S | S | N=CHOEt | −63.698 |
| 1-19 | —CH2CHMe— | H | S | S | NHMe | −63.709 |
| 1-20 | —CH2CH2— | CH3 | S | S | NH2 | |
| 1-21 | —CH2CH2— | CH3 | S | SO | NH2 | |
| 1-22 | —CH2CH2— | CH3** | S | SO | NH2 | |
| 1-23 | —CH2CH2— | CH3 | SO | SO | NH2 | |
| 1-24 | —CH2CH2— | CH3 | S | S | N=CHOEt | |
| 1-25 | —CH2CH2— | CH3 | S | S | NHMe | |
| 1-26 | —CH2CH2— | CH3 | S | SO | NHMe | |
| 1-27 | —CH2CH2— | CH3** | S | SO | NHMe | |
| 1-28 | —CH2CH2— | CH3 | S | S | N=CMe(OEt) | |
| 1-29 | —CH2CH2— | CH3 | S | S | NHEt | |
| 1-30 | —CH2CH2— | CH3 | S | S | NHC(OEt)2Me | |
| 1-31 | —CH(Me)CH(Me)— | CH3 | S | S | NH2 | |
| 1-32 | —CH2CH2— | CH3 | S | S | NHiPr | |
| 1-33 | —CH(Me)CH(Me)— | CH3 | S | SO | NH2 | |
| 1-34 | —CH(Me)CH(Me)— | CH3** | S | SO | NH2 | |
| 1-35 | —CH2CH2— | CH3 | SO | S | NHiPr | |
| 1-36 | —CH2CHMe— | CH3 | S | S | NH2 | |
| 1-37 | —CH2CHMe— | CH3 | S | S | N=CHOEt | |
| 1-38 | —CH2CHMe— | CH3 | S | S | NHMe | |
| 1-39 | —CH2CH2— | CF3 | S | S | NH2 | |
| 1-40 | —CH2CH2— | CF3 | S | SO | NH2 | |
| 1-41 | —CH2CH2— | CF3** | S | SO | NH2 | |
| 1-42 | —CH2CH2— | CF3 | SO | SO | NH2 | |
| 1-43 | —CH2CH2— | CF3 | S | S | N=CHOEt | |
| 1-44 | —CH2CH2— | CF3 | S | S | NHMe | |
| 1-45 | —CH2CH2— | CF3 | S | SO | NHMe | |
| 1-46 | —CH2CH2— | CF3** | S | SO | NHMe | |
| 1-47 | —CH2CH2— | CF3 | S | S | N=CMe(OEt) | |
| 1-48 | —CH2CH2— | CF3 | S | S | NHEt | |
| 1-49 | —CH2CH2— | CF3 | S | S | NHC(OEt)2Me | |
| 1-50 | —CH(Me)CH(Me)— | CF3 | S | S | NH2 | |
| 1-51 | —CH2CH2— | CF3 | S | S | NHiPr | |
| 1-52 | —CH(Me)CH(Me)— | CF3 | S | SO | NH2 | |
| 1-53 | —CH(Me)CH(Me)— | CF3** | S | SO | NH2 | |
| 1-54 | —CH2CH2— | CF3 | SO | S | NHiPr | |
| 1-55 | —CH2CHMe— | CF3 | S | S | NH2 | |
| 1-56 | —CH2CHMe— | CF3 | S | S | N=CHOEt | |
| 1-57 | —CH2CHMe— | CF3 | S | S | NHMe | |
| 1-58 | —CH2CH2— | CF3 | S | S | H | |
| 1-59 | —CH2CH2— | CF3 | S | S | Br | |
| 1-60 | —CH2CH2— | CF3 | S | S | SMe | |
| 1-61 | Et, Et | H | S | S | NH2 | −64.226 |
| 1-62 | Et, Et | H | S | SO | NH2 | |
| 1-63 | Et, Et | CH3 | S | S | NH2 | |
| 1-64 | Et, Et | CH3 | S | SO | NH2 | |
| 1-65 | Et, Et | CH3 | SO | SO | NH2 | |
| 1-66 | Et, Et | H | O | S | NH2 | |
| 1-67 | Et, Et | CH3 | S | S | NH2 | |
| 1-68 | Et, Et | CF3 | S | S | NH2 | |
| 1-69 | Et,Et | CF3 | SO | S | NH2 | |
| 1-70 | —CH2CH2— | H | O | S | NH2 | |
| 1-71 | —CH2CH2— | CH3 | O | S | NH2 | |
| 1-72 | —CH2CH2— | CF3 | O | S | NH2 | |
| 1-73 | —CH2CH2— | H | S | S | N(Me)CH2CH2SCH3 | |
| 1-74 | Me, Me | H | S | S | NH2 | |
| 1-75 | Me, Me | H | S | SO | NH2 | |
| 1-76 | Me, Me | CH3 | S | S | NH2 | |
| 1-77 | Me, Me | CH3 | S | SO | NH2 | |
| 1-78 | Me, Me | CH3 | SO | SO | NH2 | |
| 1-79 | Me, Me | H | O | S | NH2 | |
| 1-80 | Me, Me | CH3 | S | S | NH2 | |
| 1-81 | Me, Me | CF3 | S | S | NH2 | |
| 1-82 | Me, Me | CF3 | SO | S | NH2 | |

TABLE I-continued

Compounds of formula I in which the substituents have the following meanings:
$R_1$ is —CN, $R^5$ is —CF$_3$, $R^6$ is —Cl, W is =C(Cl)—

| Cpd No. | R$^2$ & R$^3$ | R$^4$ | X | Y | Z | Mp or $^{19}$F-NMR |
|---|---|---|---|---|---|---|
| 1-83 | —CH2CH2— | H | S | S | N(Me)CH=CH2 | |
| 1-84 | —CH2CH2— | H | S | S | NHCH2CH=CH2 | |
| 1-85 | —CH2-CH2— | H | S | SO | NHCH2CCH | |
| 1-86 | —CH2CH2— | H | S | S | N(Me)CH2CH=CH2 | |
| 1-87 | —CH2CH2— | H | S | S | N(Me)CH2CH2CH(SMe)2 | |
| 1-88 | —CH2CH2— | CF3 | S | S | NHCCH | |
| 1-89 | —CH2CH2— | CF3 | S | S | N(Me)CCH | |
| 1-90 | —CH2CH2— | H | S | S | N(Me)CH2CH(SMe)2 | |
| 1-91 | —CH2CH2— | H | S | S | N(Me)CH2CH2CH=NOEt | |
| 1-92 | —CH2CH2— | H | S | S | N(Me)CH2CH2CH=NNHCOMe | |
| 1-93 | —CH2CH2CH2— | H | S | S | NH2 | −64.231 |
| 1-94 | —CH2CH2CH2— | CF3 | S | S | NHCCH | |
| 1-94 | —CH2CH2CH2— | CF3 | S | S | N(Me)CCH | |
| 1-96 | —CH2CH2CH2— | H | S | S | N(Me)CH2CH(SMe)2 | |
| 1-97 | —CH2CH2CH2— | H | S | S | N(Me)CH2CH2CH=NOEt | |
| 1-98 | —CH2CH2CH2— | H | S | S | N(Me)CH2CH2CH=NNHCOMe | |
| 1-99 | —CH2CH2— | H | S | SO | N(Me)CH2CH=N—NH—CO—NH(4-OCF3Ph) | |
| 1-100 | —CH2CH2CH2— | H | SO | SO | N(Me)CH2CH=N—NH—CO—NH(4-OCF3Ph) | |

**represents diastereomer of the previously described compound.

TABLE 2

Compounds of formula I in which the substituents have the following meanings:
$R^1$ is —CSNH$_2$, $R^5$ is —CF$_3$, $R^6$ is —Cl, W is =C(Cl)—

| Cpd No. | R$^2$ & R$^3$ | R$^4$ | X | Y | Z | Mp or $^{19}$F-NMR |
|---|---|---|---|---|---|---|
| 2-1 | —CH2CH2— | H | S | S | NH2 | −63.725 |
| 2-2 | —CH2CH2— | H | S | SO | NH2 | −63.758 |
| 2-3 | —CH2CH2— | H** | S | SO | NH2 | |
| 2-4 | —CH2CH2— | H | SO | SO | NH2 | |
| 2-5 | —CH2CH2— | H | S | S | N=CHOEt | |
| 2-6 | —CH2CH2— | H | S | S | NHMe | −63.634 |
| 2-7 | —CH2CH2— | H | S | SO | NHMe | −63.650 |
| 2-8 | —CH2CH2— | H** | S | SO | NHMe | |
| 2-9 | —CH2CH2— | H | S | S | N=CMe(OEt) | |
| 2-10 | —CH2CH2— | H | S | S | NHEt | |
| 2-11 | —CH2CH2— | H | S | S | NHC(OEt)2Me | |
| 2-12 | —CH(Me)CH(Me)— | H | S | S | NH2 | −63.725 |
| 2-13 | —CH2CH2— | H | S | S | NHiPr | |
| 2-14 | —CH(Me)CH(Me)— | H | S | SO | NH2 | −63.742 |
| 2-15 | —CH(Me)CH(Me)— | H** | S | SO | NH2 | |
| 2-16 | —CH2CH2— | H | SO | S | NHiPr | |
| 2-17 | —CH2CHMe— | H | S | S | NH2 | |
| 2-18 | —CH2CHMe— | H | S | S | N=CHOEt | |
| 2-19 | —CH2CHMe— | H | S | S | NHMe | |
| 2-20 | —CH2CH2— | CH3 | S | S | NH2 | |
| 2-21 | —CH2CH2— | CH3 | S | SO | NH2 | |
| 2-22 | —CH2CH2— | CH3** | S | SO | NH2 | |
| 2-23 | —CH2CH2— | CH3 | SO | SO | NH2 | |
| 2-24 | —CH2CH2— | CH3 | S | S | N=CHOEt | |
| 2-25 | —CH2CH2— | CH3 | S | S | NHMe | |
| 2-26 | —CH2CH2— | CH3 | S | SO | NHMe | |
| 2-27 | —CH2CH2— | CH3** | S | SO | NHMe | |
| 2-28 | —CH2CH2— | CH3 | S | S | N=CMe(OEt) | |
| 2-29 | —CH2CH2— | CH3 | S | S | NHEt | |
| 2-30 | —CH2CH2— | CH3 | S | S | NHC(OEt)2Me | |
| 2-31 | —CH(Me)CH(Me)— | CH3 | S | S | NH2 | |
| 2-32 | —CH2CH2— | CH3 | S | S | NHiPr | |

TABLE 2-continued

Compounds of formula I in which the substituents have the following meanings:
R¹ is —CSNH₂, R⁵ is —CF₃, R⁶ is —Cl, W is =C(Cl)—

| Cpd No. | R² & R³ | R⁴ | X | Y | Z | Mp or $^{19}$F-NMR |
|---|---|---|---|---|---|---|
| 2-33 | —CH(Me)CH(Me)— | CH3 | S | SO | NH2 | |
| 2-34 | —CH(Me)CH(Me)— | CH3** | S | SO | NH2 | |
| 2-35 | —CH2CH2— | CH3 | SO | S | NHiPr | |
| 2-36 | —CH2CHMe— | CH3 | S | S | NH2 | |
| 2-37 | —CH2CHMe— | CH3 | S | S | N=CHOEt | |
| 2-38 | —CH2CHMe— | CH3 | S | S | NHMe | |
| 2-39 | —CH2CH2— | CF3 | S | S | NH2 | |
| 2-40 | —CH2CH2— | CF3 | S | SO | NH2 | |
| 2-41 | —CH2CH2— | CF3** | S | SO | NH2 | |
| 2-42 | —CH2CH2— | CF3 | SO | SO | NH2 | |
| 2-43 | —CH2CH2— | CF3 | S | S | N=CHOEt | |
| 2-44 | —CH2CH2— | CF3 | S | S | NHMe | |
| 2-45 | —CH2CH2— | CF3 | S | SO | NHMe | |
| 2-46 | —CH2CH2— | CF3** | S | SO | NHMe | |
| 2-47 | —CH2CH2— | CF3 | S | S | N=CMe(OEt) | |
| 2-48 | —CH2CH2— | CF3 | S | S | NHEt | |
| 2-49 | —CH2CH2— | CF3 | S | S | NHC(OEt)2Me | |
| 2-50 | —CH(Me)CH(Me)— | CF3 | S | S | NH2 | |
| 2-51 | —CH2CH2— | CF3 | S | S | NHiPr | |
| 2-52 | —CH(Me)CH(Me)— | CF3 | S | SO | NH2 | |
| 2-53 | —CH(Me)CH(Me)— | CF3** | S | SO | NH2 | |
| 2-54 | —CH2CH2— | CF3 | SO | S | NHiPr | |
| 2-55 | —CH2CHMe— | CF3 | S | S | NH2 | |
| 2-56 | —CH2CHMe— | CF3 | S | S | N=CHOEt | |
| 2-57 | —CH2CHMe— | CF3 | S | S | NHMe | |
| 2-58 | —CH2CH2— | CF3 | S | S | H | |
| 2-59 | —CH2CH2— | CF3 | S | S | Br | |
| 2-60 | —CH2CH2— | CF3 | S | S | SMe | |
| 2-61 | Et, Et | H | S | S | NH2 | |
| 2-62 | Et, Et | H | S | SO | NH2 | |
| 2-63 | Et, Et | CH3 | S | S | NH2 | |
| 2-64 | Et, Et | CH3 | S | SO | NH2 | |
| 2-65 | Et, Et | CH3 | SO | SO | NH2 | |
| 2-66 | Et, Et | H | O | S | NH2 | |
| 2-67 | Et, Et | CH3 | S | S | NH2 | |
| 2-68 | Et, Et | CF3 | S | S | NH2 | |
| 2-69 | Et, Et | CF3 | SO | S | NH2 | |
| 2-70 | —CH2CH2— | H | O | S | NH2 | |
| 2-71 | —CH2CH2— | CH3 | O | S | NH2 | |
| 2-72 | —CH2CH2— | CF3 | O | S | NH2 | |
| 2-73 | —CH2CH2— | H | S | S | N(Me)CH2CH2SCH3 | |
| 2-74 | Me, Me | H | S | S | NH2 | |
| 2-75 | Me, Me | H | S | SO | NH2 | |
| 2-76 | Me, Me | CH3 | S | S | NH2 | |
| 2-77 | Me, Me | CH3 | S | SO | NH2 | |
| 2-78 | Me, Me | CH3 | SO | SO | NH2 | |
| 2-79 | Me, Me | H | O | S | NH2 | |
| 2-80 | Me, Me | CH3 | S | S | NH2 | |
| 2-81 | Me, Me | CF3 | S | S | NH2 | |
| 2-82 | Me, Me | CF3 | SO | S | NH2 | |
| 2-83 | —CH2CH2— | H | S | S | N(Me)CH=CH2 | |
| 2-84 | —CH2CH2— | H | S | S | NHCH2CH=CH2 | |
| 2-85 | —CH2-CH2— | H | S | SO | NHCH2CCH | |
| 2-86 | —CH2CH2— | H | S | S | N(Me)CH2CH=CH2 | |
| 2-87 | —CH2CH2— | H | S | S | N(Me)CH2CH2CH(SMe)2 | |
| 2-88 | —CH2CH2— | CF3 | S | S | NHCCH | |
| 2-89 | —CH2CH2— | CF3 | S | S | N(Me)CCH | |
| 2-90 | —CH2CH2— | H | S | S | N(Me)CH2CH(SMe)2 | |
| 2-91 | —CH2CH2— | H | S | S | N(Me)CH2CH2CH=NOEt | |
| 2-92 | —CH2CH2— | H | S | S | N(Me)CH2CH2CH=NNHCOMe | |
| 2-93 | —CH2CH2CH2— | H | S | S | N(Me)CH2CH2CH(SMe)2 | |
| 2-94 | —CH2CH2CH2— | CF3 | S | S | NHCCH | |
| 2-94 | —CH2CH2CH2— | CF3 | S | S | N(Me)CCH | |
| 2-96 | —CH2CH2CH2— | H | S | S | N(Me)CH2CH(SMe)2 | |
| 2-97 | —CH2CH2CH2— | H | S | S | N(Me)CH2CH2CH=NOEt | |
| 2-98 | —CH2CH2CH2— | H | S | S | N(Me)CH2CH2CH=NNHCOMe | |
| 2-99 | —CH2CH2— | H | S | SO | N(Me)CH2CH=N—NH—CO—NH(4-OCF3 Ph) | |
| 2-100 | —CH2CH2CH2— | H | SO | SO | N(Me)CH2CH=N—NH—CO—NH(4-OCF3 Ph) | |

**represents diastereomer of the previously described compound.

TABLE 3

Compounds of formula I in which the substituents have the following meanings
$R^1$ is —CN, $R^2$ and $R^3$ are —CH$_2$CH$_2$—, $R^6$ is —Cl, $R^5$ is —CF$_3$

| Cpd No. | W | $R^4$ | X | Y | Z | Mp or $^{19}$F-NMR |
|---|---|---|---|---|---|---|
| 3-1 | C-NHEt | H | S | S | NH2 | −64.098 |
| 3-2 | C-NHEt | H | S | SO | NH2 | −64.109 |
| 3-3 | C-N(Et)2 | H | S | S | NH2 | −63.915 |
| 3-4 | C-N(Me)2 | H | SO | SO | NH2 | |
| 3-5 | C-N(Me)2 | H | S | S | N=CHOEt | |
| 3-6 | C-NHMe | H | S | S | NHMe | |
| 3-7 | C-NHMe | H | S | SO | NHMe | |
| 3-8 | C-NHEt | CF3 | S | SO | NHMe | |
| 3-9 | C-NH2 | H | S | S | N=CMe(OEt) | |
| 3-10 | C-N(Me)CH2CH2SCH3 | H | S | S | NHEt | |
| 3-11 | C-N(Me)2 | H | S | S | NHC(OEt)2Me | |
| 3-12 | N | H | S | S | NH2 | |
| 3-13 | C-NHEt | H | S | S | NHiPr | |
| 3-14 | N | H | S | SO | NH2 | |
| 3-15 | N | CH3 | S | S | NH2 | |
| 3-16 | C-NHEt | H | SO | S | NHiPr | |
| 3-17 | N | CH3 | S | SO | NHMe | |
| 3-18 | N | CF3 | S | S | NH2 | |
| 3-19 | N | CF3 | SO | S | NH2 | |
| 3-20 | C-NHCH2CF3 | CH3 | S | S | NH2 | |
| 3-21 | C-N(Me)CH2CF3 | CH3 | S | SO | NH2 | |
| 3-22 | C-NHCH2CF3 | CH3 | S | SO | NH2 | |
| 3-23 | C-NHCH2CF3 | CH3 | SO | SO | NH2 | |
| 3-24 | C-N(Me)CH=CH2 | CH3 | S | S | N=CHOEt | |
| 3-25 | C-N(Me)CH=CH2 | CH3 | S | S | NHMe | |
| 3-26 | C-N(Me)CH=CH2 | CH3 | S | SO | NHMe | |
| 3-27 | C-N(Me)CH2CH=CH2 | CH3 | S | SO | NHMe | |
| 3-28 | C-NHEt | CH3 | S | S | N=CMe(OEt) | |
| 3-29 | C-N(Et)2 | CH3 | S | S | NHEt | |
| 3-30 | C-NHMe | CH3 | S | S | NH2 | |

According to a further feature of the present invention there is provided a method for the control of pests at a locus which comprises applying thereto an effective amount of a compound of formula I or a salt thereof. For this purpose, the said compound is normally used in the form of a pesticidal composition (i.e. in association with compatible diluents or carriers and/or surface active agents suitable for use in pesticidal compositions), for example as hereinafter described.

The term "compound of the invention" as used hereinafter embraces a compound of formula I as defined above and a pesticidally acceptable salt thereof.

One aspect of the present invention as defined above is a method for the control of pests at a locus. The locus includes, for example, the pest itself, the place (plant, field, forest, orchard, waterway, soil, plant product, or the like) where the pest resides or feeds, or a place susceptible to future infestation by the pest. The compound of the invention may therefore be applied directly to the pest, to the place where the pest resides or feeds, or to the place susceptible to future infestation by the pest.

As is evident from the foregoing pesticidal uses, the present invention provides pesticidally active compounds and methods of use of said compounds for the control of a number of pest species which includes: arthropods, especially insects or mites, or plant nematodes. The compound of the invention may thus be advantageously employed in practical uses, for example, in agricultural or horticultural crops, in forestry, in veterinary medicine or livestock husbandry, or in public health.

The compounds of the invention may be used for example in the following applications and on the following pests:

For the control of soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

In the protection of stored, products, for example cereals, including grain or flour, groundnuts, animal feedstuffs, timber or household goods, e.g. carpets and textiles, compounds of the invention are useful against attack by arthropods, more especially beetles, including weevils, moths or mites, for example *Ephestia* spp. (flour moths), *Anthrenus* spp. (carpet beetles), *Tribolium* spp. (flour beetles), *Sitophilus* spp. (grain weevils) or *Acarus* spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, *Reticulitermes* spp., *Heterotermes* spp., *Coptotermes* spp.

Moreover it has been found that the compounds of the invention exhibit high insecticidal action against insects that destroy technical materials.

As example and preferably—but not limiting—the following insects are named:
Beetles such as *Hylotrupes bajulus, Chlorophorus pilosis, Anobium punctatum, Xestobium rufovillosum, Ptilinus pecti-* cornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec. Tryptodendron spec. Apate monachus, Bostrychus capucins, Heterobostrychus brunneus, Sinoxylon spec. Dinoderus minutus;

Hymenoptera such as Sirex juvencus, Urocerus gigas, Urocerus gigas taignus, Urocerus augur;

Termites such as Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;

Silverfish such as Lepisma saccharina.

Within the present context technical materials are understood to mean non-living materials such as preferably plastics, adhesives, glues, paper and cardboard, leather, wood, wood fabrication products and paints.

At the same time the compounds of the invention can be used for protection against fouling of objects, especially ships' hulls, screens, nets, buildings, wharfs and signal installations that come into contact with sea or brackish water.

Moreover, the compounds of the invention can be used in combination with other active compounds as anti-fouling agents.

The active compounds are suitable for the control of zoopests in household, hygiene and storage protection, especially insects, arachnids and mites that appear in enclosed spaces such as apartments, factory halls, offices, vehicle cabins, etc. They can be used alone or in combination with other active compounds and auxiliaries in household insecticidal products for the control of these pests. They are active against sensitive and resistant species as well as against all development stages. These pests include:

The order Scorpionidea e.g. Buthus occitanus.

The order Acarina e.g. Argas persicus, Argas reflexus, Bryobia ssp., Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.

The order Araneae e.g Avicularidae, Araneidae.

The order Opiliones e.g Pseudoscorpiones chelifer, Pseudoscorpiones cheiridium, Opiliones phalangium.

The order Isopoda e.g Oniscus asellus, Porcellio scaber.

The order Diplopoda e.g. Blaniulus guttulatus, Polydesmus spp.

The order Chilopoda e.g. Geophilus spp.

The order Zygentoma e.g. Ctenolepisma spp., Lepisma saccharina, Lepismodes inquilinus.

The order der Blattaria e.g. Blatta orientalies, Blattella germanica, Blattella asahinai, Leucophaea maderae, Panchlora spp., Parcoblatta spp., Periplaneta australasiae, Periplaneta americana, Periplaneta brunnea, Periplaneta fuliginosa, Supella longipalpa.

The order Saltatoria e.g. Acheta domesticus.

The order Dermaptera e.g. Forficula auricularia.

The order Isoptera e.g. Kalotermes spp., Reticulitermes spp.

The order Psocoptera e.g. Lepinatus spp., Liposcelis spp.

The order Coleoptera e.g. Anthrenus spp., Attagenus spp., Dermestes spp., Latheticus oryzae, Necrobia spp., Ptinus spp., Rhizopertha dominica, Sitophilus granarius, Sitophilus oryzae, Sitophilus zeamais, Stegobium paniceum.

The order Diptera e.g. Aedes aegypti, Aedes albopictus, Aedes taeniorhynchus, Anopheles spp., Calliphora erythrocephala, Chrysozona pluvialis, Culex quinquefasciatus, Culex pipiens, Culex tarsalis, Drosophila spp., Fannia canicularis, Musca domestica, Phlebotomus spp., Sarcophaga carnaria, Simulium spp., Stomoxys calcitrans, Tipula paludosa.

The order Lepidoptera e.g. Achroia grisella, Galleria mellonella, Plodia interpunctella, Tinea cloacella, Tinea pellionella, Tineola bisselliella.

The order Siphonaptera e.g. Ctenocephalides canis, Ctenocephalides felis, Pulex irritans, Tunga penetrans, Xenopsylla cheopis.

The order Hymenoptera e.g. Camponotus herculeanus, Lasius fuliginosus, Lasius niger, Lasius umbratus, Monomorium pharaonis, Paravespula spp., Tetramorium caespitum.

The order Anoplura e.g. Pediculus humanus capitis, Pediculus humanus corporis, Pemphigus spp., Phylloera vastatrix, Phthirus pubis.

The order Heteroptera e.g. Cimex hemipterus, Cimex lectularius, Rhodinus prolixus, Triatoma infestans.

The use in the household insecticidal sector is carried out alone or in combination with other suitable active compounds such as phosphates, carbamates, pyrethroids, neonicotinoids, growth regulators or active compounds from other known classes of insecticides.

Use is carried out with aerosols, non-pressurised spray agents, e.g. pump and dusting sprays, nebulisers, misters, foamers, gels, evaporation products with evaporation platelets of cellulose or plastic, liquid evaporators, gel and membrane evaporators, propeller-driven evaporators, non-energy or passive evaporation systems, fly papers, fly traps, and fly gels, as granulates or dusts, in scatter bait or bait stations.

In agriculture against adults, larvae and eggs of Lepidoptera (butterflies and moths), e.g. Heliothis spp. such as Heliothis virescens (tobacco budworm), Heliothis armigera and Heliothis zea. Against adults and larvae of Coleoptera (beetles) e.g. Anthonomus spp. e.g. grandis (cotton boll weevil), Leptinotarsa decemlineata (Colorado potato beetle), Diabrotica spp. (corn rootworms). Against Heteroptera (Hemiptera and Homoptera) e.g. Psylla spp., Bemisia spp., Trialeurodes spp., Aphis spp., Myzus spp., Megoura viciae, Phylloxera spp., Nephotettix spp. (rice leaf hoppers), Nilaparvata spp.

Against Diptera e.g. Musca spp. Against Thysanoptera such as Thrips tabaci. Against Ortlioptera such as Locusta and Schistocerca spp., (locusts and crickets) e.g. Gryllus spp., and Acheta spp. for example, Blatta orientalis, Periplaneta americana, Blatella germanica, Locusta migratoria migratorioides, and Schistocerca gregaria. Against Collembola e.g. Periplaneta spp. and Blatella spp. (roaches).

Against arthropods of agricultural significance such as Acari (mites) e.g. Tetranychus spp., and Panonychus spp.

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. M. incognita).

In the field of veterinary medicine or livestock husbandry or in the maintenance of public health against arthropods which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. soft-bodied ticks including Argasidae spp. e.g. Argas spp. and Ornithodorus spp. (e.g. Ornithodorus moubata); hard-bodied ticks including Ixodidae spp., e.g. Boophilus spp. e.g. Boophilus microplus, Rhipicephalus spp. e.g. Rhipicephalus appendiculatus and Rhipicephalus sanguineus; mites (e.g. Damalinia spp.); fleas (e.g. Ctenocephalides spp. e.g. Ctenocephalides felis (cat flea) and Ctenocephalides canis (dog flea)); lice e.g. *Menopon* spp.; Diptera (e.g. *Aedes* spp., *Anopheles* spp., *Musca* spp., *Hypoderma* spp.); Hemiptera; Dictyoptera (e.g. *Periplaneta* spp., *Blatella* spp.); Hymenoptera; for example against infections of the gastrointestinal tract caused by parasitic nematode worms, for example members of the family Trichostrongylidae.

In a preferred aspect of the invention the compounds of formula I are used for the control of parasites of animals. Preferably the animal to be treated is a domestic companion animal such as a dog or a cat.

The parasites to be controlled include for example:

The order Anoplurida e.g. *Haematopinus* spp., *Linognathus* spp., *Pediculus* spp., *Phtirus* spp., *Solenopotes* spp.

The order Mallophagida and the suborders Amblycerina and Ischnocerina e.g. *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

The order Diptera and the suborders Nematocerina and Brachycerina e.g. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

The order Siphonapterida e.g. *Pulex* spp., *Ctenocephalides* spp., *Xenopsylla* spp., *Ceratophyllus* spp.

The order Heteropterida e.g. *Cimex* spp., *Triatoma* spp., *Rhodnius* spp., *Panstrongylus* spp.

The order Blattarida e.g *Blatta orientalis, Periplaneta americana, Blattela germanica, Supella* spp.

The subclass Acari (Acarina) and the order Meta- and Mesostigmata e.g. *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

The order Actinedida (Prostigmata) and Acaridida (Astigmata) e.g. *Acarapis* spp., *Cheyletiella* spp., *Ornithocheyletia* spp., *Myobia* spp., *Psorergates* spp., *Denodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compounds of the invention of structure (1) are also suitable for the control of arthropods that affect agricultural animals such as cattle, sheep, goats, horses, pigs, donkeys, camels, buffalo, rabbits, chickens, turkeys, ducks, geese, bees, other domestic animals such as dogs, cats, cage birds, aquarium fish as well as so-called experimental animals such as hamsters, guinea pigs, rats and mice. By control of these arthropods death rates and performance loss (in meat, milk, wool, hides, eggs, honey, etc.) will be reduced so that a more economic and simpler animal husbandry is possible by the use of the compounds of the invention.

The use of the active compounds in veterinary sector and animal husbandry is carried out by known means by enteric administration in the form of, for example, tablets, capsules, drinks, drenches, granulates, pastes, boli, the feed-through process, suppositories, by parenteral administration by, for example, injection (intramuscular, subcutaneous, intravenous, interperitoneal, among others), implants, by nasal application, by dermal administration in the form of, for example, dipping, spraying, pour-on and spot-on, washing, powdering and with the help of appliances containing the active compound such as collars, ear markers, tail markers, limb bands, halters, marking devices, etc.

During use in cattle, poultry, domestic animals, etc., the active compounds of structure (I) can be used as formulations (for example, powder, emulsions, flowable agents) that contain the active compounds in an amount of 1 to 80 wt. %, directly or after 100 to 10,000 times dilution or as a chemical bath.

In a further aspect of the invention the compounds of formula I or salts or compositions thereof are used for the preparation of a veterinary medicament.

A further feature of the invention thus relates to the use of a compound of formula I or a salt thereof, or of a composition thereof, for the control of pests as already mentioned above:

The above named pests include for example:
the order Anoplura (Phthiraptera) e.g. *Damalinia* spp., *Haematopinus* spp., *Linognathus* spp., *Pediculus* spp., *Trichodectes* spp.

The class of Arachnida e.g. *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Lxodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

The class of Bivalva e.g. *Dreissena* spp.

The order Chilopoda e.g. *Geophilus* spp., *Scutigera* spp.

The order Coleoptera e.g. *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Syniphyletes* spp., *Tenebrio molitor, Tribolium* spp., *Trogoderma* spp., *Tychius* spp., *Xylotrechus* spp., *Zabrus* spp.

The order Collembola e.g. *Onychiurus armatus*.

The order Dermaptera e.g. *Forficula auricularia*.

The order Diplopoda e.g. *Blaniulus guttulatus*.

The order Diptera e.g. *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

The class Gastropoda e.g. *Arion* spp., *Biomphalaria* spp., *Bulinus* spp., *Deroceras* spp., *Galba* spp., *Lymnaea* spp., *Oncomelania* spp., *Succinea* spp.

The class of Helminths e.g. *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuellebomi*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

In addition protozoa such as Eimeria may be controlled.

The order Heteroptera e.g. *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

The order Homoptera e.g. *Acyrtliosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaplies* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

The order Hymenopterae.g. *Diprion* spp., *Hoplocampa* spp., *Lasius* spp., *Monomorium pharaonis*, *Vespa* spp.

The order Isopoda e.g. *Armadillidium vulgare*, *Oniscus asellus*, *Porcellio scaber*.

The order Isopterae.g. *Reticulitermes* spp., *Odontotermes* spp.

The order Lepidoptera e.g. *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

The order Orthoptera e.g. *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

The order Siphonaptera e.g. *Ceratophyllus* spp., *Xenopsylla cheopis*.

The order Symphyla e.g. *Scutigerella immaculata*.

The order Thysanoptera e.g. *Baliothrips biformis*, *Enneothrips flavens*, *Frankliniella* spp., *Heliothrips* spp., *Hercinothrips femoralis*, *Kakotbrips* spp., *Rhipiphorothrips cruentatus*, *Scirtothrips* spp., *Taeniothrips cardamoni*, *Thrips* spp.

The order Thysanura e.g. *Lepisma saccharina*.

The plant parasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

The compounds of structure (I) of the invention are characterised particularly by strong action against aphids (e.g. *Aphis gossypii* and *Myzus persicae*), beetle larvae (e.g. *Phaedon cochleariae*), butterfly caterpillars (e.g. *Plutella xylostella*, *Spodoptera exigua* and *Spodoptera frugiperda*).

The compounds of the invention can optionally also be used in certain concentrations or application amounts as herbicides, safeners, growth regulators, or as agents for improving plant properties or as microbiocides, for example as fungicides, antimycotics, bactericides, viricides (including agents against viroids) or as agents against MLO (Mycoplasma-like organism) and RLO (Rickettsia-like organism). They may also be optionally used as intermediates or precursors for the synthesis of further active compounds.

According to the invention all plants and plant parts can be treated. Plants are hereby understood to mean all plants and plant populations such as desirable and undesirable wild plants or cultigens (including naturally occurring cultigens).

Cultigens can be plants that can be obtained by conventional breeding and optimisation methods or by biotechnology or genetic engineering methods or combinations of these methods, including transgenic plants and including plant varieties that are protectable or not protectable by plant varieties protection rights. Plant parts are understood to be all above ground and below ground parts and organs of the plants such as scion, leaf, blossom and root, including, for example, leaves, needles, stalks, stems, blossoms, fruiting bodies, fruits and seed as well as roots, bulbs, rhizomes. Harvest crops as well as vegetative and generative reproduction material, for example cuttings, bulbs, rhizomes, shoots and seed also belong to plant parts.

In practical use for the control of arthropods, especially insects or mites, or helminths, especially nematode pests of plants, a method, for example, comprises applying to the plants or to the medium in which they grow an effective amount of a compound of the invention. For such a method, the compound of the invention is generally applied to the locus in which the arthropod or nematode infestation is to be controlled at an effective rate in the range of about 2 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha.

When a pest is soil-borne, the active compound generally in a formulated composition, is distributed evenly over the area to be treated (ie, for example broadcast or band treatment) in any convenient manner and is, applied at rates from about 10 g ai/ha to about 400 g ai/ha, preferably from about 50 g ai/ba to about 200 g ai/ha ("ai" means "active ingredient"). When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The compound of the invention can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compound of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compound of the invention and methods of use thereof are of particular value in the control of arthropods or helminths which are injurious to, or spread or act as vectors of diseases domestic animals, for example those hereinbefore mentioned, and more especially in the control of ticks, mites, lice, fleas, midges, or biting, nuisance or myiasis flies.

The compounds of the invention are particularly useful in controlling arthropods or helminths which are present inside domestic host animals or which feed in or on the skin or suck the blood of the animal, for which purpose they may be administered orally, parenterally, percutaneously or topically.

The compositions hereinafter described for application to growing crops or crop growing loci or as a seed dressing may, in general, alternatively be employed in the protection of stored products, household goods, property or areas of the general environment. Suitable means of applying the compounds of the invention include:
to growing crops as foliar sprays (for example as an in-furrow spray), dusts, granules, fogs or foams or also as suspensions of finely divided or encapsulated compositions as soil or root treatments by liquid drenches, dusts, granules, smokes or foams; to seeds of crops via application as seed dressings, e.g. by liquid slurries or dusts;
to animals infested by or exposed to infestation by arthropods or helminths, by parenteral, oral or topical application of compositions in which the active ingredient exhibits an immediate and/or prolonged action over a period of time against the arthropods or helminths, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;
to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water.

The compounds of formula I are particularly useful for the control of parasites of animals when applied orally, and in a further preferred aspect of the invention the compounds of formula Ia or Ib are used for the control of parasites of animals by oral application. The compounds of the formula I or salts thereof may be administered before, during or after meals. The compounds of the formula I or salts thereof may be mixed with a carrier and/or foodstuff.

The compound of the formula I or salt thereof is administered orally in a dose to the animal in a dose range generally from 0.1 to 500 mg/kg of the compound of the formula Ia or Ib or salt thereof per kilogram of animal body weight (mg/kg).

The frequency of treatment of the animal, preferably the domestic animal to be treated by the compound of the formula I or salt thereof is generally from about once per week to about once per year, preferably from about once every two weeks to once every three months.

The compounds of the invention may be administered most advantageously with another parasiticidally effective material, such as an endoparasiticide, and/or an ectoparasiticide, and/or an endectoparasiticide. For example, such compounds include macrocyclic lactones such as avermectins or milbemycins e.g., ivermectin, pyratel or an insect growth regulator such as lufenuron or methoprene.

The compounds of the formula I can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

All plants that have received by genetic engineering modification genetic material that imparts particularly advantageous valuable properties ("traits") to these plants belong to the transgenic (obtained by genetic engineering) plants or plant varieties to be preferably treated in accordance with the invention. Examples of such properties are improved plant growth, increased tolerance toward high or low temperatures, increased tolerance toward drought or toward water or soil salt content, improved blossoming performance, simplified harvesting, accelerated ripening, increased harvest yields, improved quality and/or nutritional value of the crop, better storage life and/or processing of the crop. Further and particularly emphasised examples of such properties are increased resistance of the plants toward zoopests and microbial pests, such as toward insects, mites, pathogenic plant fungi, bacteria and/or viruses as well as an increased tolerance of the plants toward certain herbicides. Examples of such transgenic plants are the important cultigens such as cereals (wheat, rice), maize, soy, potato, sugar beet, tomato, peas, and other vegetable varieties, cotton, tobacco, rape as well as fruit plants (with the fruits apple, pear, citrus fruits and grapes), whereby maize, soy, potato, cotton, tobacco and rape are especially emphasised. Properties ("traits") especially emphasised are the increased tolerance of the plants toward insects, arachnids, nematodes and gastropods through the toxins formed in the plants, especially those that are produced in the plants (hereinafter known as "Bt plants") by the genetic material from *Bacillus thuringiensis* (e.g. from the genes CryIA(a), CryIA(b), CryIA(c), CryIIA, CryIIIA, CryIIB2, Cry9c Cry2Ab, Cry3Bb and CryIF as well as their combinations). Also particularly emphasised as properties ("traits") is the increased resistance of plants toward fungi, bacteria and viruses through systemically acquired resistance (SAR), systemin, phytoalexine, elicitors and resistance genes and correspondingly expressed proteins and toxins. Further particularly emphasised properties ("traits") are the increased tolerance of the plants to certain active herbicidal compounds, for example imidazolinones, sulphonylureas, glyphosate or phosphinotricin (e.g. "PAT"-gene). The respective genes imparting the desired properties ("traits") can also occur in the transgenic plants in combination with each other. Examples of such "Bt plants" are maize varieties, cotton varieties, soy varieties and potato varieties that are marketed under the trade marks YIELD GARD® (e.g. maize, cotton, soy), KnockOut® (e.g. maize), StarLink® (e.g. maize), Bollgard® (cotton), Nucotn® (cotton) and NewLeaf® (potato). Examples of herbicide tolerant plants are maize varieties, cotton varieties and soy varieties that are marketed under the trade marks Roundup Ready® (tolerance toward glyphosate, e.g. maize, cotton, soy), Liberty Link® (tolerance toward phosphinotricin, e.g. rape), IMI® (tolerance toward imidazolinones) and STS® (tolerance toward sulphonyl ureas, e.g. maize). Also mentioned as herbicide resistant (conventionally bred for herbicide tolerance) plants are those varieties marketed under the name Clearfield® (e.g. maize). Naturally these statements also apply to plant varieties developed or marketed in the future with these genetic properties ("traits") or those developed in the future.

The use in economically important transgenic crops of useful plants and ornamentals is preferred, for example of cereals such as wheat, barley, rye, oats, millet, rice, cassaya and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore also relates to the use of compounds of the formula I for controlling harmful organisms in transgenic crop plants.

According to a further feature of the present invention there is provided a pesticidal composition comprising one or more compounds of the invention as defined above, in association with, and preferably homogeneously dispersed in one or more compatible pesticidally acceptable diluents or carriers and/or surface active agents (i.e. diluents or carriers and/or surface active agents of the type generally accepted in the art as being suitable for use in pesticidal compositions and which are compatible with compounds of the invention).

In practice, the compounds of the invention most frequently form parts of compositions. These compositions can be employed to control arthropods, especially insects, or plant nematodes or mites. The compositions may be of any type known in the art suitable for application to the desired pest in any premises or indoor or outdoor area. These compositions contain at least one compound of the invention as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

The compounds of the invention, in their commercially available formulations and in the use forms prepared from these formulations may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms.

Fungicides:
Nucleic Acid Synthesis Inhibitors
  benalaxyl, benalaxyl-M, bupirimate, chiralaxyl, clozylacon, dimethirimol, ethirimol, furalaxyl, hymexazol, metalayl, metalaxyl-M, ofurace, oxadixyl, oxolinic acid
Inhibitors of Mitosis and Cell Division benomyl, carbendazim, diethofencarb, fuberidazole, pencycuron, thiabendazole, thiophanate-methyl, zoxamis Inhibitor of respiratory complex I
  diflumetorim Inhibitors of Respiratory Complex II
  boscalid, carboxin, fenfuram, flutolanil, furametpyr, mepronil, oxycarboxin, penthiopyrad, thifluzamide Inhibitor of Respiratory Complex III
  azoxystrobin, cyazofamide, dimoxystrobin, enestrobin, famoxadone, fenamidone, fluoxastrobin, kresoximm-ethyl, metominostrobin, orysastrobin, pyraclostrobin, picoxystrobin Decouplers
  dinocap, fluazinam Inhibitors of ATP Production
  fentin acetate, fentin chloride, fentin hydroxide, silthiofam Inhibitor of Amino Acid and Protein Biosynthesis
  andoprim, blasticidin-S, cyprodinil, kasugamycin, kasugamycin hydrochloride hydrate, mepanipyrim, pyrimethanil Inhibitors of Signal Transduction
  fenpiclonil, fludioxonil, quinoxyfen Inhibitors of Fat and Membrane Synthesis
  chlozolinate, iprodione, procymidone, vinclozolin
  ampropylfos, potassium ampropylfos, edifenphos, iprobenfos (IBP), isoprothiolane, pyrazophos
  tolclofos-methyl, biphenyl
  iodocarb, propamocarb, propamocarb hydrochloride Inhibitors of Ergosterol Biosynthesis
  fenhexamide,
  azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidol, nuarimol, pyrifenox, triforin, pefurazoate, prochloraz, triflumizole, viniconazole,
  aldimorph, dodemorph, dodemorph acetate, fenpropimorph, tridemorph, fenpropidin, spiroxamine,
  naftifin, pyributicarb, terbinafin Inhibitors of Cell Wall Synthesis
  benthiavalicarb, bialaphos, dimethomorph, flumorph, iprovalicarb, polyoxins, polyoxorim, validamycin A Inhibitors of Melanin Biosynthesis
  capropamide, diclocymet, fenoxanil, phtalide, pyroquilon, tricyclazole Resistance Induction
  acibenzolar-S-methyl, probenazole, tiadinil Multisite
  captafol, captan, chlorothalonil, copper salts: copper hydroxide, copper naphthenate, copper oxychloride, copper sulphate, copper oxide, oxine-copper and Bordeaux mixture, dichlofluanid, dithianon, dodin, dodin freie base, ferbam, fluorofolpet, guazatin, guazatin acetate, iminoctadin, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism
  amibromdol, benthiazole, bethoxazin, capsimycin, carvone, quinoline methionate, chloropicrin, cufraneb, cyflufenamide, cymoxanil, dazomet, debacarb, diclomezine, dichlorophen, dicloran, difenzoquat, difenzoquat methyl sulphate, diphenylamine, ethaboxam, ferimzone, flumetover, flusulfamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylpbenol and salts, piperalin, propanosin-sodium, proquinazid, pyrroInitrin, quintozen, tecloftalam, tecnazen, triazoxido, trichlamide, zarilamide and 2,3,5,6-tetrachloro-4-(methylsulphonyl)pyridine, N-(4-chloro-2-nitrophenyl)N-ethyl-4-methylbenzenesulphonamide, 2-amino-4-methyl-N-phenyl-5-thiazole carboxamide, 2-chloro-N-(2,3-dihydro-1,1,3-trimethyl-1H-inden-4-yl)-3-pyridine carboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)-phenyl]ethyliden]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridine dicarbonitriel, methyl 2-[[[cyclopropyl[(4-methoxyphenyl) imino]methyl]thio]methyl]-.alpha.-(methoxymethylen)-benzacetate, 4-chloro-alpha-propinyloxy-N-[2-[3-methoxy-4-(2-propinyloxy)phenyl]ethyl]-benzacetamide, (2S)—N-[2-[4-[[3-(4-chlorophenyl)-t-propinyl]oxy]-3-methoxyphenyl]ethyl]-3-methyl-2-[(methylsulphonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl) [1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-{(Z)-[(cyclopropylmethoxy) imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3(1fluoro-2-phenylethyl)oxy]phenyl ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-Methoxy-3-pyridinyl)-cyclopropane carboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chlor-2-methylphenoxy)-5-fluoropyrimidin-4-yl]oxy}phenyl)-2-(methoxyimino)-N-methylacetamide Bactericides:
bronopol, dichlorophen, nitrapyrin, nickel dimethyldithiocarbamate, kasugamycin, octhilinon, furan carboxylic acid, oxytetracyclin, probenazol, streptomycin, tecloftalam, copper sulphate and other copper preparations.

Insecticide/Acaricide/Nematicide:
Acetylcholinesterase (AChE) Inhibitors
  carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates,
for example acephate, azamethiphos, azinphos (-methyl, -ethyl), aromophos-ethyl, aromfenvinfos (-methyl), autathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphone, dialifos, diazinone, dichlofenthione, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fentliion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidone, phosphocarb, Phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium Channel Modulators/Voltage-Dependent Sodium Channel Blockers
pyrethroids,
for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permiethrin (cis-, trans-), phenotbrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, trans-fluthrin, ZXI 8901, pyrethrins (pyrethrum)

DDT oxadiazines,
for example indoxacarb

Acetylcholine Receptor Agonists/Antagonists
chloronicotinyls,
for example acetamiprid, clothianidin, dinotefuran, imidacloprid, nitenpyram, nithiazine, thiacloprid, thiamethoxam
nicotine, bensultap, cartap Acetylcholine Receptor Modulators
Spinosynes,
for example spinosad GABA Controlled Chloride Channel Antagonists
Organochlorinee,
for example camphechlior, chlordane, endosulfan, gamma-HCH, HCH, heptachlor, lindane, methoxychlor Fiproles,
for example acetoprole, ethiprole, fipronil, pyrafluprole, pyriprole, vaniliprole Chloride Channel Activators
Mectins,
for example avermectin, emamectin, emamectin benzoate, ivermectin, milbemycin Juvenile hormone mimetics,
for example diofenolan, epofenonane, fenoxycarb, hydroprene, kinoprene, methoprene, pyriproxifen, triprene Ecdysone Agonists/Disruptors
diacylhydrazines,
for example chromafenozide, halofenozide, methoxyfenozide, tebufenozide Inhibitors of Chitin Biosynthesis
Benzoylureas,
for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
buprofezin
cyromazine Inhibitors of Oxidative Phosphorylation, ATP Disruptors
diafenthiuron
organotin compounds,
for example azocyclotin, cyhexatin, fenbutatin-oxide Decouplers of Oxidative Phosphorylation by Interruption of H-Proton Gradients
pyrrole,
for example chlorfenapyr
dinitrophenols,
for example binapacyrl, dinobuton, dinocap, DNOC Site I Electron Transport Inhibitors
METI's,
for example fenazaquin, fenpyroximate, pyrimidifen, pyridaben, tebufenpyrad, tolfenpyrad
hydramethylnon
dicofol Site II Electron Transport Inhibitors
rotenones Site III Electron Transport Inhibitors
acequinocyl, fluacrypyrim Microbial Disruptors of Insect Intestinal Membrane
*Bacillus thuringiensis* strains Inhibitors of Fat Synthesis
tetronic acids,
for example spirodiclofen, spiromesifen
tetramic acids,
for example spirotetramat (CAS-Reg.-No.: 203313-25-1) and 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8)

carboxamides,
for example flonicamid
octopaminergic agonists,
for example amitraz Inhibitor of Magnesium-Stimulated ATPase,
propargite
benzoic acid dicarboxamides,
for example flubendiamide Nereistoxin analogous,
for example thiocyclam hydrogen oxalate, thiosultap-sodium Agonists of the Ryanodin Receptor,
    benzoic acid dicarboxamides,
    for example flubendiamide
Biologicals, Hormones or Pheromones
    azadirachtin, *Bacillus* spec., *Beauveria* spec., codlemone, *Metarrhizium* spec., *Paecilomyces* spec., thuringiensin, *Verticillium* spec.
Active Compounds with Unknown or Non-Specific Mode of Action
    fumigants,
    for example aluminium phosphide, methyl bromide, sulphuryl fluoride
    feeding inhibitors,
    for example cryolite, flonicamid, pymetrozine
    mite growth inhibitors,
    for example clofentezine, etoxazole, hexythiazox
    amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds such as herbicides, fertilisers, growth regulators, safeners, semiochemicals or also with agents for improving plant properties is also possible.

The active compounds of the invention can also be present in their normal commercial formulations when used as insecticides as well as in the application forms prepared from these formulations in admixture with synergists. Synergists are compounds through which the activity of the active compound can be increased without the added synergist itself having to be active.

The active compounds of the invention can also be present in their normal commercial formulations when used as insecticides as well as in the application forms prepared from these formulations in admixture with inhibitors that reduce degradation of the active compound after use in the environment of the plants, on the surface of the plants or in plant tissues.

The abovementioned components for combinations are known active substances, many of which are described in Ch. R Worthing, S. B. Walker, The Pesticide Manual, 12$^{th}$ Edition, British Crop Protection Council, Farnham 2000.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

Suitable as solid carriers are:
for example, ammonium salts and natural mineral powders such a kaolin, clays, talc, chalk, quartz attapulgite, montmorillonite or diatomaceous earth, and synthetic mineral powders such as highly dispersed silica, aluminium oxide and silicates, suitable as carriers for granulates are: for example crushed and fractionated natural minerals such as calcite, marble, pumice, sepiolite, dolomite as well as synthetic granulates of inorganic and organic flours as well as granulates from organic materials such as paper, sawdust, coconut shells, maize ears and tobacco stalks; suitable as emulsifiers and foaming agents are; for example non-ionogenic and anionic emulsifiers such as polyoxyethylene fatty acid esters, polyoxyethylene fatty alcohol ethers, for example alkylarylpolyglycol ethers, alkylsulphonates, alkylsulphates, arylsulphonates and protein hydrolysates; suitable as dispersant are non-ionic and/or ionic materials, for example from the class of alcohol-POE and/or POP ethers, acid- and/or POP or POE esters, alkyl-aryl- and/or POP or POE ethers, fat- and/or POP or POE adducts, POE- and/or POP-polyol derivates, POE- and/or POP-sorbitan or sugar adducts, alkyl or aryl sulphates, sulphonates and phosphates or the respective PO ether adducts. In addition suitable oligo- or polymers, for example starting from vinylic monomers, of acrylic acid, from EO and/or PO alone or in combination with, for example (poly)alcohols or (poly)amines. In addition lignin and its sulphonic acid derivatives, simple and modified celluloses, aromatic and/or aliphatic sulphonic acids as well as their adducts with formaldehyde can be used.

Deposit builders such as carboxymethylcellulose, natural and synthetic powdery, granular or latex-like polymers can be used in the formulations, such as gum arabic, polyvinyl alcohol, polyvinyl acetate as well as natural phospholipids such a cephalins and lecithins and synthetic phospholipids. The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

For their agricultural application, the compounds of the invention are therefore generally in the form of compositions, which are in various solid or liquid forms.

Solid forms of compositions which can be used are dusting powders (with a content of the compound of the invention, ranging up to 80%), wettable powders or granules (including water dispersible granules), particularly those obtained by extrusion, compacting, impregnation of a granular carrier, or granulation starting from a powder (the content of the compound of the invention, in these wettable powders or granules being between about 0.5 and about 80%). Solid homogenous or heterogenous compositions containing one or more compounds of the invention, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compound or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient is thoroughly mixed in a suitable blender with additional substances which may be impregnated on the porous filler and is ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod or plant nematode pests usually contain from about 0.00001% to about 95%, more particularly from about 0.0005% to about 50% by weight of one or more compounds of the invention, or of total active ingredients (that is to say the compounds of the invention, together with other substances toxic to arthropods or plant nematodes, synergists, trace elements or stabilizers).

The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of the invention. For administration to animals orally or parenterally, including percutaneously solid or liquid compositions, these normally contain from about 0.1% to about 90% by weight of one or more compounds of the invention. Medicated feedstuffs normally contain from about 0.001% to about 3% by weight of one or more compounds of the invention. Concentrates or supplements for mixing with feedstuffs normally contain from about 5% to about 90%, preferably from about 5% to about 50%, by weight of one or more compounds of the invention. Mineral salt licks normally contain from about 0.1% to about 10% by weight of one or more compounds of formula I or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of the invention. Suitable concentrations in treated waters are between about 0.0001 ppm and about 20 ppm, more particularly about 0.001 ppm to about 5.0 ppm. of one or more compounds of the invention, and may be used therapeutically in fish farming with appropriate exposure times. Edible baits may contain from about 0.01% to about 5%, preferably from about 0.01% to about 1.0%, by weight, of one or more compounds of the invention.

When administered to vertebrates parenterally, orally or by percutaneous or other means, the dosage of compounds of the invention, will depend upon the species, age, or health of the vertebrate and upon the nature and degree of its actual or potential infestation by arthropod or helminth pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A-2M illustrate compositions for use against arthropods, especially mites or insects, or plant nematodes, which comprise, as active ingredient, compounds of the invention, such as those described in preparative examples. The compositions described in EXAMPLES 2A-2M can each be diluted to give a sprayable composition at concentrations suitable for use in the field. Generic chemical descriptions of the ingredients (for which all of the following percentages are in weight percent), used in the composition EXAMPLES 2A-2M exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan $NO_2$ | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

Example 2A

A water soluble concentrate is prepared with the composition as follows:

| Active ingredient | 7% |
|---|---|
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

Example 2B

An emulsifiable concentrate (EC) is prepared with the composition as follows:

| Active ingredient | 25%(max) |
|---|---|
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

Example 2C

A wettable powder (WP) is prepared with the composition as follows:

| Active ingredient | 40% |
|---|---|
| Arylan S | 2% |
| Darvan $NO_2$ | 5% |
| Celite PF | 53% |

The ingredients are mixed and ground in a hammer-mill to a powder with a particle size of less than 50 microns.

Example 2D

An aqueous-flowable formulation is prepared with the composition as follows:

| Active ingredient | 40.00% |
|---|---|

-continued

| | | |
|---|---|---|
| Ethylan BCP | 1.00% | |
| Sopropon T360. | 0.20% | |
| Ethylene glycol | 5.00% | |
| Rhodigel 230. | 0.15% | |
| Water | 53.65% | |

The ingredients are intimately mixed and are ground in a bead mill until a mean particle size of less than 3 microns is obtained.

Example 2E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a bead mill until a mean particle size of less than 3 microns is obtained.

Example 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

Example 2G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

Example 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

Example 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

Example 2J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, by spraying or dipping, or by oral administration in drinking water, to control the arthropods.

Example 2K

A slow release bolus composition is formed from granules containing the following components in varying percentages (similar to those described for the previous compositions) depending upon need:
Active ingredient
Density agent
Slow-release agent
Binder The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods.

Example 2L

A slow release composition in the form of granules, pellets, brickettes or the like can be prepared with compositions as follows:
Active ingredient 0.5 to 25%
Polyvinyl chloride 75 to 99.5%
Dioctyl phthalate (plasticizer)
The components are blended and then formed into suitable shapes by melt-extrusion or molding. These composition are useful, for example, for addition to standing water or for fabrication into collars or eartags for attachment to domestic animals to control pests by slow release.

Example 2M

A water dispersible granule is prepared with the composition as follows:

| Active ingredient | 85%(max) |
|---|---|
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

Methods of Pesticidal Use

The following representative test procedure, using compounds of the invention, was conducted to determine the parasiticidal activity of compounds of the invention.

Method A: Screening Method to Test Systemicity of Compounds Against Ctenoceplialides felis (Cat Flea)

A test container was filled with 10 adults of *Ctenocephalides felis*. A glass cylinder was closed on one end with parafilm and placed on top of the test container. The test compound solution was then pipetted into bovine blood and added to the glass cylinder. The treated *Ctenocephalides felis* were held in this artificial dog test (blood 37° C., 40-60% relative humidity; *Ctenocephalides felis* 20-22° C., 40-60% relative humidity) and assessment performed at 24 and 48 hours after application.

Compound numbers 1-1, 1-2, and 1-3 gave at least 70% control of *Ctenocephalides felis* at a test concentration of 50 ppm or less.

Method B: Screening Method to Test Contact Activity Against *Rhipicephalus sanguineus* (Brown Dog Tick)

Solutions of the test compounds were dropped onto filter paper, dried and the filter paper placed into test tubes and infested with 20-30 larvae (L1) of *Rhipicephalus sanguineus* and the tubes closed with a clip. The treated *Rhipicephalus sanguineus* were held in a climate chamber (25° C., 90% RH) and the percentage efficacy assessed 24 hours after application in comparison with the untreated control.

Compounds 1-61, 1-70, and 1-93 provided at least 50% of control with the test concentration at 1,000 ppm.

What is claimed is:
1. A compound of formula I or a pesticidally acceptable salt thereof, wherein

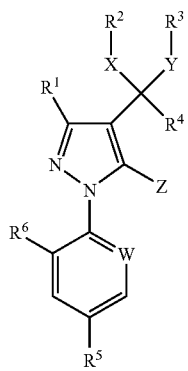

(I)

W is =CH—, =CR$^7$— or =C(NR$^8$R$^9$)—,
R$^7$ is halogen, alkyl or haloalkyl,
R$^8$ and R$^9$ are independently of one another hydrogen or alkyl;
R$^1$ is cyano or —CS—NH$_2$,
R$^2$ and R$^3$ can be linked together to form a five to eight membered heterocyclic or unsaturated ring system;
R$^4$ is hydrogen, (C$_1$-C$_3$)-alkyl or (C$_1$-C$_3$)-haloalkyl,
R$^5$ is (C$_1$-C$_3$)-haloalkyl, (C$_1$-C$_3$)-haloalkoxy, halogen or —SF$_5$, and
R$^6$ is hydrogen, halogen, nitro or —NR$^{16}$R$^{17}$,
R$^{16}$ and R$^{17}$ are independently of one another hydrogen or alkyl,
X is —S—, —SO—, or —SO$_2$—,
Y is —O—, —S—, —SO—, or —SO$_2$—,
Z is —NR$^{18}$R$^{19}$,
R$^{18}$ is hydrogen or alkyl, wherein the alkyl is optionally substituted by one or more halogens,
R$^{19}$ is hydrogen, —CO—O—R$^{24}$, —CO—R$^{25}$ or which —CO—O—R$^{24}$, —CO—R$^{25}$ or alkyl groups are optionally substituted by one or more halogen,
R$^{24}$ and R$^{25}$ independently of one another are alkyl or haloalkyl or R$^{18}$ and R$^{19}$ together with the attached N-atom form an imine group —N=CR$^{18a}$R$^{19a}$ or an iminoether group —N=CR$^{18a}$(OR$^{19a}$),
R$^{18a}$ is hydrogen, alkyl, and
R$^{19a}$ is alkyl,
which groups R$^{18a}$ and R$^{19a}$ independently of one another are optionally substituted by one or more halogen, hydroxyl, oxo, cyano, nitro, alkyl, haloalkyl, alkoxy, haloalkoxy, or alkylthio groups or by amino, which is optionally substituted by alkyl, alkenyl, or alkynyl groups.

2. A compound as claimed in claim 1, wherein W is =CR$^7$— or =C(NR$^8$R$^9$)— or a pesticidally acceptable salt thereof.

3. A compound as claimed in claim 2, wherein W is =C(halogen)-, =C(NH$_2$)—, or a pesticidally acceptable salt thereof.

4. A compound as claimed in claim 2, wherein R$^7$ is chlorine or fluorine or a pesticidally acceptable salt thereof.

5. A compound as claimed in claim 1, wherein R$^1$ is cyano.

6. A compound as claimed in claim 1, wherein R$^2$ and R$^3$ are linked together to form a five to eight membered heterocyclic or unsaturated ring system with two sulfur ring atoms or with one sulfur and one oxygen ring atoms.

7. A compound as claimed in claim 1, wherein R$^4$ is hydrogen.

8. A compound as claimed in claim 7, wherein R$^4$ is (C$_1$-C$_3$)-alkyl.

9. A compound as claimed in claim 1, wherein $R^5$ is $(C_1-C_3)$-haloalkyl, $(C_1-C_3)$-haloalkoxy or —$SF_5$ or a pesticidally acceptable salt thereof.

10. A compound as claimed in claim 9, wherein $R^5$ is $(C_1-C_3)$-haloalkyl.

11. A compound as claimed in claim 1, wherein $R^6$ is hydrogen or halogen.

12. A compound as claimed in claim 1, wherein X and Y are each —S— or —SO— or —$SO_2$.

13. A compound as claimed in claim 1, wherein Y is —S— or a pesticidally acceptable salt thereof.

14. A compound as claimed in claim 1, wherein Z is $NH_2$ and $R^1$ is cyano, or a pesticidally acceptable salt thereof.

15. A compound as claimed in claim 1 or a pesticidally acceptable salt thereof, wherein:
   $R^1$ is cyano;
   $R^4$ is hydrogen,
   $R^5$ is —$CF_3$, —$OCF_3$, —$SF_5$ or halogen,
   $R^6$ is halogen,
   W is =C(halogen) or,
   X is —S—, —SO— or —$SO_2$—,
   Y is —O—, —S—, —SO— or —$SO_2$—,
   Z is $NR^{18}R^{19}$,
   $R^{18}$ is hydrogen or $(C_1-C_4)$-alkyl, and
   $R^{19}$ is hydrogen or $(C_1-C_4)$-alkyl.

16. A compound as claimed in claim 1, wherein
   $R^1$ is —CN,
   $R^2$, $R^3$, X and Y are linked together to form 1,3-dithiolane or 1,3-dithiane ring systems, wherein the sulfur atoms may be unoxidized or in an oxidized form,
   $R^4$ is hydrogen, and
   W is =C(halogen).

17. A compound as claimed in claim 1, wherein
   $R^1$ is —CN,
   $R^4$ is $(C_1-C_3)$-alkyl, and
   W is =C(halogen).

18. A compound as claimed in claim 1, wherein
   $R^1$ is —CN,
   $R^2$, $R^3$, X and Y are linked together to form 1,3-dithiolane or 1,3-dithiane ring systems, wherein the sulfur atoms may be unoxidized or in an oxidized form,
   $R^4$ is hydrogen,
   Z is —$NR^{18}R^{19}$, and
   W is =C(halogen).

19. A compound as claimed in claim 1, wherein
   $R^1$ is CN,
   $R^2$, $R^3$, X and Y are linked together to form 1,3-dithiolane or 1,3-dithiane ring systems, wherein the sulfur atoms may be unoxidized or in an oxidized form,
   $R^4$ is hydrogen,
   Z is —$NR^{18}R^{19}$,
   W is =C(halogen)-,
   $R^5$ is $CF_3$, and
   $R^6$ is halogen.

20. A compound as claimed in claim 15, wherein
   $R^1$ is —CN,
   $R^2$, $R^3$, X and Y are linked together to form 1,3-dithiolane or 1,3-dithiane ring systems, wherein the sulfur atoms may be unoxidized or in an oxidized form,
   Z is $NH_2$,
   W is =C(Cl),
   $R^5$ is —$CF_3$, or —$SF_5$, and
   $R^6$ is chloro or fluoro.

21. A compound as claimed in claim 15, wherein
   $R^1$ is —CN,
   $R^2$, $R^3$, X and Y are linked together to form 1,3-dithiolane or 1,3-dithiane ring systems, wherein the sulfur atoms may be unoxidized or in an oxidized form,
   $R^4$ is hydrogen,
   Z is $NH_2$,
   W is =C(Cl),
   $R^5$ is —$CF_3$, and
   $R^6$ is chloro.

22. A process for preparation of compounds of formula I as claimed in claim 1 comprising reacting a compound of formula II

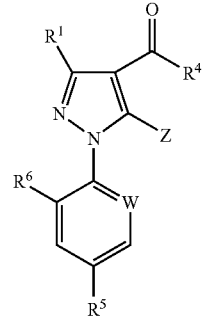

(II)

wherein $R^1$, $R^4$, $R^5$, $R^6$, W and Z are as defined in claim 1, with a compound of formula III, $$R^2—XH \text{ or } R^3—YH \text{ or } HX—R^2—R^3—YH \quad (III)$$

wherein $R^2$, $R^3$, X and Y are as defined in claim 1, in the presence of a catalyst in an organic solvent.

23. A pesticidal composition comprising as an active ingredient at least one compound of formula I according to claim 1 or a pesticidial acceptable salt thereof in combination with a pesticidally acceptable carrier.

24. A pesticidal composition according to claim 23 comprising diluents or carriers and optionally surface active agents which are compatible with said active ingredient.

25. A pesticidal composition comprising the compound of claim 21 in combination with a pesticidally acceptable carrier.

26. A method for controlling pests at a locus which comprises applying to the locus an effective amount of a compound of formula (I), according to claim 1, or a pesticidally acceptable salt thereof.

* * * * *